United States Patent
Yuan et al.

(10) Patent No.: US 8,673,646 B2
(45) Date of Patent: *Mar. 18, 2014

(54) ELECTROCHEMICAL BIOSENSOR FOR DIRECT DETERMINATION OF PERCENTAGE OF GLYCATED HEMOGLOBIN

(75) Inventors: Chong-Sheng Yuan, San Diego, CA (US); Neal K. Blue, Del Mar, CA (US); Abhijit Datta, Carlsbad, CA (US); Limin Liu, San Diego, CA (US); Lei Fang, Poway, CA (US)

(73) Assignee: General Atomics, San Diego, CA (US)

( * ) Notice: Subject to any disclaimer, the term of this patent is extended or adjusted under 35 U.S.C. 154(b) by 186 days.

This patent is subject to a terminal disclaimer.

(21) Appl. No.: 12/465,143

(22) Filed: May 13, 2009

(65) Prior Publication Data

US 2010/0025264 A1 Feb. 4, 2010

Related U.S. Application Data

(60) Provisional application No. 61/052,888, filed on May 13, 2008.

(51) Int. Cl.
 *G01N 33/72* (2006.01)
(52) U.S. Cl.
 USPC .............................. 436/67; 435/25; 205/792
(58) Field of Classification Search
 USPC ............ 204/403.01–403.15; 205/777.5, 792; 435/14, 25; 436/63, 66, 67
 See application file for complete search history.

(56) References Cited

U.S. PATENT DOCUMENTS

| | | | |
|---|---|---|---|
| 2,713,581 | A | 7/1955 | Pannone et al. |
| 4,588,684 | A | 5/1986 | Brake |
| 4,837,331 | A | 6/1989 | Yamanishi et al. |
| 4,847,195 | A | 7/1989 | Khanna et al. |
| 4,948,729 | A | 8/1990 | Piatak, Jr. et al. |
| 5,013,647 | A | 5/1991 | Town et al. |
| 5,030,563 | A | 7/1991 | Schendel et al. |
| 5,120,420 | A | 6/1992 | Nankai et al. |
| 5,137,821 | A | 8/1992 | Sagai et al. |
| 5,171,670 | A | 12/1992 | Kronenberg et al. |
| 5,196,314 | A | 3/1993 | Town et al. |
| 5,229,286 | A | 7/1993 | Jarsch et al. |
| 5,244,796 | A | 9/1993 | Levy et al. |
| 5,308,770 | A | 5/1994 | Jarsch et al. |

(Continued)

FOREIGN PATENT DOCUMENTS

| | | |
|---|---|---|
| CN | 1456680 | 11/2003 |
| EP | 0 121 352 A1 | 10/1984 |

(Continued)

OTHER PUBLICATIONS

Allgrove, J. et al. (1988). Fructosamine or Glycated Haemoglobin as a Measure of Diabetic Control? *Archives of Disease in Childhood* 63:418-422.

(Continued)

*Primary Examiner* — J. Christopher Ball
(74) *Attorney, Agent, or Firm* — Morrison & Foerster LLP

(57) ABSTRACT

The invention provides electrochemical biosensors for direct determination of percentage of glycated hemoglobin in blood samples without the need of a separated measurement of total hemoglobin content in blood samples. The invention provides methods for using the electrochemical biosensors.

56 Claims, 7 Drawing Sheets

(56) References Cited

U.S. PATENT DOCUMENTS

| | | | |
|---|---|---|---|
| 5,312,759 A | 5/1994 | Hama et al. | |
| 5,320,732 A | 6/1994 | Nankai et al. | |
| 5,344,770 A | 9/1994 | Hitomi et al. | |
| 5,385,846 A * | 1/1995 | Kuhn et al. | 205/777.5 |
| 5,509,410 A | 4/1996 | Hill et al. | |
| 5,628,890 A | 5/1997 | Carter et al. | |
| 5,681,529 A | 10/1997 | Taguchi et al. | |
| 5,682,884 A | 11/1997 | Hill et al. | |
| 5,710,248 A | 1/1998 | Grose | |
| 5,712,138 A | 1/1998 | Kato et al. | |
| 5,789,221 A | 8/1998 | Kato et al. | |
| 5,820,551 A | 10/1998 | Hill et al. | |
| 5,824,527 A | 10/1998 | Kato et al. | |
| 5,856,104 A | 1/1999 | Chee et al. | |
| 5,879,921 A | 3/1999 | Cherry et al. | |
| 5,885,811 A | 3/1999 | Hansen | |
| 5,914,250 A | 6/1999 | Hansen | |
| 5,948,659 A | 9/1999 | Kato et al. | |
| 5,948,665 A | 9/1999 | Matsukawa et al. | |
| 5,972,294 A | 10/1999 | Smith et al. | |
| 5,972,671 A | 10/1999 | Kato et al. | |
| 5,972,745 A | 10/1999 | Kalter et al. | |
| 5,985,591 A | 11/1999 | Yonehara et al. | |
| 6,008,006 A | 12/1999 | Torrens et al. | |
| 6,069,297 A | 5/2000 | Luzzatto et al. | |
| 6,127,138 A | 10/2000 | Ishimaru et al. | |
| 6,127,345 A | 10/2000 | Burnham | |
| 6,143,164 A | 11/2000 | Heller et al. | |
| 6,194,200 B1 | 2/2001 | Rose et al. | |
| 6,270,637 B1 | 8/2001 | Crismore et al. | |
| 6,329,161 B1 | 12/2001 | Heller et al. | |
| 6,352,835 B1 | 3/2002 | Komori et al. | |
| 6,380,380 B1 | 4/2002 | Kaufman | |
| 6,451,574 B1 | 9/2002 | Brode, III et al. | |
| RE37,919 E | 12/2002 | Kronenberg et al. | |
| 6,514,720 B2 * | 2/2003 | Komori et al. | 435/25 |
| 6,863,800 B2 | 3/2005 | Karinka et al. | |
| 7,153,666 B2 | 12/2006 | Yuan et al. | |
| 7,235,378 B2 | 6/2007 | Yonehara et al. | |
| 7,276,146 B2 | 10/2007 | Wilsey | |
| 7,276,147 B2 | 10/2007 | Wilsey | |
| 7,381,539 B2 | 6/2008 | Yonehara et al. | |
| 7,855,079 B2 | 12/2010 | Yuan et al. | |
| 7,943,385 B2 | 5/2011 | Yuan et al. | |
| 8,318,501 B2 | 11/2012 | Yuan et al. | |
| 8,338,184 B2 | 12/2012 | Yuan et al. | |
| 2002/0009779 A1 | 1/2002 | Meyers et al. | |
| 2003/0032077 A1* | 2/2003 | Itoh et al. | 435/14 |
| 2003/0162242 A1 | 8/2003 | Yonehara | |
| 2003/0211564 A1* | 11/2003 | Qian et al. | 435/23 |
| 2004/0063213 A1 | 4/2004 | Hirai et al. | |
| 2004/0166560 A1 | 8/2004 | Mueller et al. | |
| 2004/0171130 A1 | 9/2004 | Yokoi et al. | |
| 2005/0014935 A1 | 1/2005 | Yuan et al. | |
| 2005/0255453 A1 | 11/2005 | Qian et al. | |
| 2007/0099283 A1 | 5/2007 | Mueller et al. | |
| 2008/0096230 A1* | 4/2008 | Yuan et al. | 435/7.8 |
| 2008/0176296 A1 | 7/2008 | Zelder et al. | |
| 2008/0241880 A1 | 10/2008 | Yuan et al. | |
| 2008/0299597 A1 | 12/2008 | Yuan et al. | |
| 2009/0090623 A1 | 4/2009 | Chuang et al. | |
| 2011/0189712 A1 | 8/2011 | Yuan et al. | |
| 2011/0250627 A1 | 10/2011 | Yuan et al. | |

FOREIGN PATENT DOCUMENTS

| | | |
|---|---|---|
| EP | 0 121 352 B1 | 10/1984 |
| EP | 0 127 958 A2 | 12/1984 |
| EP | 0 127 958 A3 | 12/1984 |
| EP | 0 127 958 B1 | 12/1984 |
| EP | 0 127 958 B2 | 12/1984 |
| EP | 0 189 918 A2 | 8/1986 |
| EP | 0 189 918 A3 | 8/1986 |
| EP | 0 189 918 B1 | 8/1986 |
| EP | 0 196 864 A2 | 10/1986 |
| EP | 0 196 864 A3 | 10/1986 |
| EP | 0 239 931 A2 | 10/1987 |
| EP | 0 239 931 A3 | 10/1987 |
| EP | 0 239 931 B1 | 10/1987 |
| EP | 0 351 891 A2 | 1/1990 |
| EP | 0 351 891 A3 | 1/1990 |
| EP | 0 351 891 B1 | 1/1990 |
| EP | 0 186 643 A1 | 7/1996 |
| EP | 0 186 643 B1 | 7/1996 |
| EP | 0 821 064 A2 | 1/1998 |
| EP | 0 821 064 A3 | 1/1998 |
| EP | 0 821 064 B1 | 1/1998 |
| EP | 1 223 224 A1 | 7/2002 |
| EP | 1 223 224 B1 | 7/2002 |
| EP | 1 304 385 A1 | 4/2003 |
| EP | 1 542 015 A1 | 6/2005 |
| EP | 1 614 746 A1 | 1/2006 |
| EP | 1 651 759 B1 | 5/2006 |
| GB | 738585 | 10/1955 |
| GB | 1 513 488 | 6/1978 |
| WO | WO-89/03886 A1 | 5/1989 |
| WO | WO-90/12113 A1 | 10/1990 |
| WO | WO-93/06125 A1 | 4/1993 |
| WO | WO-96/28556 A2 | 9/1996 |
| WO | WO-96/28556 A3 | 9/1996 |
| WO | WO-00/28041 A1 | 5/2000 |
| WO | WO-01/47968 A1 | 7/2001 |
| WO | WO-01/68694 A1 | 9/2001 |
| WO | WO-01/90325 A2 | 11/2001 |
| WO | WO-01/90325 A3 | 11/2001 |
| WO | WO-01/90378 A1 | 11/2001 |
| WO | WO-01/98472 A1 | 12/2001 |
| WO | WO-02/20795 A1 | 3/2002 |
| WO | WO-02/064760 A2 | 8/2002 |
| WO | WO-02/064760 A3 | 8/2002 |
| WO | WO-02/072634 A2 | 9/2002 |
| WO | WO-02/072634 A3 | 9/2002 |
| WO | WO-03/042389 A1 | 5/2003 |
| WO | WO-2005/017136 A1 | 2/2005 |
| WO | WO-2007/094354 A1 | 8/2007 |
| WO | WO 2008/013874 A1 * | 1/2008 |
| WO | WO-2008/013874 A1 | 1/2008 |
| WO | WO-2009/140343 A1 | 11/2009 |

OTHER PUBLICATIONS

Amendment After Final Action mailed on Jun. 22, 2006, for U.S. Appl. No. 10/622,893, filed Jul. 17, 2003, 12 pages.

Amendment in Response to Non-Final Office Action mailed on Nov. 25, 2005, for U.S. Appl. No. 10/622,893, filed Jul. 17, 2003, 25 pages.

Amendment in Response to Non-Final Office Action submitted on Feb. 19, 2010, for U.S. Appl. No. 11/881,179, filed Jul. 25, 2007, 16 pages.

Amendment in Response to Non-Final Office Action submitted on Jul. 19, 2010, for U.S. Appl. No. 11/881,179, filed Jul. 25, 2007, 10 pages.

Amendment in Response to Non-Final Office Action submitted on Nov. 4, 2010, for U.S. Appl. No. 12/120,122, filed May 13, 2008, 9 pages.

Anonymous. (1972). "IUPAC-IUB Commission on Biochemical Nomenclature Symbols for Amino-Acid Derivatives and Peptides Recommendations (1971)," *Biochemistry* 11(9):1726-1732.

Armbuster, D.A. (1987). "Frutosamine: Structure, Analysis, and Clinical Usefulness," *Clin. Chem.* 33(12):2153-2163.

Baker, J. et al. (1991). "Fructosamine Test-Plus, a Modified Fructosamine Assay Evaluated," *Clin. Chem.* 37(4):552-556.

Bastin, P. et al. (1996). "A Novel Epitope Tag System to Study Protein Targeting and Organelle Biogenesis in *Trypanosoma brucei*," *Mol. Biochem. Parasitology* 77:235-239.

Baynes, J.W. et al. eds. (1989). "The Maillard Reaction in Aging, Diabetes, and Nutrition," *Progress in Clinical and Biological Resaerch*, Alan R. Liss, Inc.: New York, NY, vol. 304, pp. vii-ix, (Table of Contents Only.).

Branden, C. et al. (1991). "Prediction, Engineering, and Design of Protein Structures," in Chapter 16 in *Introduction to Protein Structure*, Garland Publishing Inc.: New York, NY, pp. 247.

(56) References Cited

OTHER PUBLICATIONS

Chen, C-F. et al. (Jul. 1998). "Expression Vector Containing an N-Terminal Epitope Tag for *Dictyostelium discoideum*," *BioTechniques* 25(1):22-24.

Communication Pursuant to Article 96(2) EPC, mailed on Aug. 29, 2006, for EP Application No. 04 778 420.2-1222, filed on Jul. 16, 2004, 3 pages.

Communication under Rule 51(4) EPC, mailed on May 31, 2007,for EP Application No. 04 778 420.2-1222, filed on Jul. 16, 2004, 5 pages.

Diazyme (Date Unknown). "Fructosyl Amino Acid Oxidoreductase (Recombinant)," Laboratories Division, General Atomics, FAOX-TE Fact Sheet, pp. 71-74.

Entry into the European Phase, filed Feb. 17, 2006, for EP Application No. 04 778 420.2-1222, 18 pages.

Fang, L. et al. (Feb. 22, 2008, e-pub. Sep. 9, 2007). "An Electrochemical Biosensor of the Ketone 3-β-hydroxybutyrate for Potential Diabetic Patient Management," *Sensors and Actuators B: Chemical* 129(2):818-825.

Final Office Action mailed on Feb. 23, 2006, for U.S. Appl. No. 10/622,893, filed Jul. 17, 2003, 10 pages.

Fossati, P. et al. (Feb. 1980). "Use of 3,5-Dichloro-2-hydroxybenzensulfonic Acid/ 4-Aminophenazone Chromogenic System in Direct Enzymic Assay of Uric Acid in Serum Urine," *Clin. Chem.* 26(2):227-231.

Frederick, K.R. et al. (Mar. 5, 1990). "Glucose Oxidase from *Aspergillus niger*," *J. Biol. Chem.* 265(7):3793-3802.

Freedictonary.com (Date Unknown). "Glycosylated Hemoglobin," located at <http://medical-dictionary.thefreedictionary.com/Hba1c>, last visited on Nov. 4, 2010, 3 pages.

GenBank Database Accession No. U82830, last updated May 15, 1997, located at <<http://www.ncbi.nlm.nih.gov/entrez/viewer.fcgi?db=nuccore&id=1769599>>, last visited on Aug. 20, 2007, two pages.

Gerhardingerm, C. et al. (Jan. 6, 1995). "Novel Degradation Pathway of Glycated Amino Acids into *Free* Fructosamine by a *Pseudomonas* sp. Soil Strain Extract," *The Journal of Biological Chemistry* 270(1):218-224.

Hardy, S.J.S. et al. (1989). "Biochemical Investigation of Protein Export in *Escherichia coli*," *J. Cell. Sci. Suppl.* 11:29-43.

Hobom, G. et al. (1995). "OmpA Fusion Proteins for Presentation of Foreign Antigens on the Bacterial Outer Membrane," *Dev. Biol. Stand.* 84:255-262.

International Preliminary Report on Patentability issued on Jan. 23, 2006, for PCT Patent Application No. PCT/US2004/022908, filed on Jul. 16, 2004, 6 pages.

International Search Report mailed on Jan. 26, 2005, for PCT Patent Application No. PCT/US2004/022908, filed on Jul. 16, 2004, 5 pages.

International Search Report mailed on Nov. 20, 2007, for PCT Application No. PCT/US2007/016774, filed on Jul. 25, 2007, 3 pages.

International Search Report mailed on Nov. 4, 2009, for PCT Patent Application No. PCT/US2009/043725, filed on May 13, 2009, 2 pages.

INVITROGEN (2002). "pBAD TOPO TA Expression Kit," p. 75.

Kouzuma, T. et al. (2002). "An Enzymatic Method for the Measurement of Glycated Albumin in Biological Samples," *Clin. Chimi. Acta.* 324:61-71.

Kühn, S. et al. (1979). "Close Vicinity of IS*1* Integration Sites in the Leader Sequence of the *gal* Operon of *E. coli*," *Mol. Gen. Genet.* 167(3):235-241.

Luo, Y-C. et al. (2006, e-pub Sep. 5, 2006). "An Amperometric Uric Acid Biosensor Based on Modified Ir-C Electrode," *Biosensors and Bioelectronics* 22:482-488.

Michiels, J. et al. (Apr. 2001). "Processing and Export of Peptide Pheromones and Bacteriocins Gram-Negative Bacteria," *Trends Microbiol.* 9(4):164-168.

Nagata, R. et al. (1995). "A Glucose Sensor Fabricated by the Screen Printing Technique," *Biosens. Bioelectron.* 10(3-4):261-267.

Nagelkerken, B. et al. (1997). "A Novel Epitope Tag for the Detection of rabGTPases," *Electrophoresis* 18:2694-2698.

Non-Final Office Action mailed on Jul. 22, 2005, for U.S. Appl. No. 10/622,893, filed Jul. 17, 2003, 15 pages.

Non-Final Office Action mailed on May 15, 2009, for U.S. Appl. No. 11/595,209, filed Nov. 8, 2006, 12 pages.

Non-Final Office Action mailed on Nov. 19, 2009, for U.S. Appl. No. 11/881,179, filed Jul. 25, 2007, 16 pages.

Non-Final Office Action mailed on May 27, 2010, or U.S. Appl. No. 11/881,179, filed Jul. 25, 2007, 13 pages.

Non-Final Office Action mailed on Aug. 4, 2010, for U.S. Appl. No. 12/120,122, filed May 13, 2008, 12 pages.

Notice of Allowance and Examiner's Amendment mailed on Aug. 10, 2006, for U.S. Appl. No. 10/622,893, filed Jul. 17, 2003, 8 pages.

Notice of Allowance mailed on Aug. 11, 2010, for U.S. Appl. No. 11/881,179, filed Jul. 25, 2007, 4 pages.

Oláh, Z. et al. (1994). "A Cloning and ε-Epitope-Tagging Insert for the Expression of Polymerase Chain Reaction-Generated cDNA Fragments in *Escherichia coli* and Mammalian Cells," *Analyt. Biochem.* 221:94-102.

Peakman, T.C. et al. (1992). "Enhanced Expression of Recombinant Proteins in Insect Cells Using a Baculovirus Vector Containing a Bacterial Leader Sequence," *Nucleic Acids Res.* 20(22):6111-6112.

Phillipou , G. et al. (1988). "Re-Evaluation of the Fructosamine Reaction," *Clin. Chem.* 34(8):1561-164.

Prickett, K.S. et al. (1989). "A Calcium-Dependent Antibody for Identification and Purification of Recombinant Proteins," *BioTechniques* 7(6):580-584.

Response to European Office Action, filed Mar. 7, 2007, for EP Application No. 04 778 420.2-1222, filed on Jul. 16, 2004, 36 pages.

Restriction Requirement mailed on Apr. 14, 2005, for U.S. Appl. No. 10/622,893, filed Jul. 17, 2003, 4 pages.

Restriction Requirement mailed on Jun. 12, 2009, for U.S. Appl. No. 11/881,179, filed Jul. 25, 2007, 7 pages.

Restriction Requirement mailed on Jun. 18, 2010, for U.S. Appl. No. 12/120,122, filed May 13, 2008, 7 pages.

Response to Restriction Requirement mailed on May 18, 2005, for U.S. Appl. No. 10/622,893, filed Jul. 17, 2003, 2 pages.

Response to Restriction Requirement submitted on Jul. 10, 2009, for U.S. Appl. No. 11/881,179, filed Jul. 25, 2007, 7 pages.

Response to Restriction Requirement submitted on Jul. 15, 2010, for U.S. Appl. No. 12/120,122, filed May 13, 2008, 6 pages.

Roesser, J.R. et al. (1991). "The Effects of Leader Peptide Sequence and Length on Attenuation Control of the *trp* Operon of *E. coli*," *Nucleic Acids Res.* 19(4):795-800.

Rosen-Margalit, I. et al. (1993). "Novel Approaches for the Use of Mediators in Enzyme Electrodes," *Biosens. Bioelectron.* 8(6):315-323.

Rüdiger, M. et al. (Jul. 1997). "Epitope Tag-Antibody Combination Useful for the Detection of Protein Expression in Prokaryotic and Eukaryotic Cells," *BioTechniques* 23(1):96-97.

Saier, M.H. et al. (1988). "Sugar Premeases of the Bacterial Phophoenolpyruvate-Dependent Phosphotransferase System: Sequence Comparisons," *FASEB J.* 2(3):199-208.

Sakaguchi, A. et al. (Jun. 1, 2003). "Development of Highly-Sensitive Fructosyl-Valine Enzyme Sensor Employing Recombinant Fructosyl Amine Oxidase," *Electrochemisty* 71(6):442-445.

Sakai, Y. et al. (1995). "Purification and Properties of Fructsyl Lysince Oxidase from *Fusarium oxysporum* S-1F4," *Biosci. Biotech. Biochem.* 59(3):487-491.

Sakurabayashi, I. et al. (2003). "New Enzymatic Assay for Glycohemoglobin," *Clinical Chemistry* 49(2):269-274.

Schleicher, E.D. et al. (1988). "Is Serum Fructosamine Assay Specific for Determination of Glycated Serum Protein?" *Clin. Chem.* 34(2):320-323.

Seffernick, J.L. et al. (Apr. 2001). "Melamine Deaminase and Atrazine Chlorohydrolase: 98 Percent Identical but Functionally Different," *J. Bacteriol.* 183(8):2405-2410.

Shaklai, N. et al. (Mar. 25, 1984). "Noenzymatic Glycosylation of Human Serum Albumin Alters Its Conformation and Function," *The Journal of Biological Chemistry* 259(6):3812-3817.

(56) References Cited

OTHER PUBLICATIONS

Sigma-Aldrich (2002). "Product No. 82452," located at <https://www.sigmaaldrich.com/cgi-bin/hsrun/Suite7/Suite/HAHTpage/Suite.HsViewHierarc . . . >, last visited on Mar. 2, 2004, 1 page.
Takahashi, M. et al. (Feb. 7, 1997). "Isolation, Purification, and Characterization of Amadoriase Isoenzymes (Fructosyl Amine-Oxygen Oxidoreductase EC 1.5.3) from *Aspergillus* sp.," *J. Biol. Chem.* 272(6):3437-3443.
Takahashi, M. et al. (May 9, 1997). "Molecular Cloning and Expression of Amadoriase Isoenzyme (Fructosyl Amine:Oxygen Oxidoreductase, EC 1.5.3) from *Aspergillus fumigatus*," *J. Biol. Chem.* 272(19):12505-12507.
Tolbert, L.M. et al. (1998). "Antibody to Eptiope Tag Induces Internalization of Human Muscarinic Subtype 1 Receptor," *J. Neurochem.* 70(1):113-119.
Tseng, C-P. et al. (1996). "Functional Expression and Characerization of the Mouse Epitope Tag-Protein Kinase C Isoforms, α,βI, βII, γ, δ, and ε," *Gene* 169:287-288.
Tsugawa, W. et al. (Dec. 1, 2001). "Fructosyl Amine Sensing Based on Prussian Blue Modified Enzyme Electrode," *Electrochemistry* 69(12):973-975.
Wang, L.-F. et al. (1996). "BTag: A Novel Six-Residue Epitope Tag for Surveillance and Purification of Recombinant Proteins," *Gene* 169(1):53-58.
Wang, J. et al. (Nov. 1, 1994). "Highly Selective Membrane-Free, Mediator-Free Glucose Biosensor," *Anal. Chem.* 66(21):3600-3603.
Wang, J. (2008, e-pub Dec. 23, 2007). "Electrochemical Glucose Biosensors," *Chem. Rev.* 108(2):814-825.
Watson, J.D. et al. (1987). *Molecular Biology of the Gene*, 4th Edition, The Benjamin/Cummings Publishing Company, Inc. pp. 224-225.
Witkowski, A. et al. (1999, e-pub. Aug. 18, 1999). "Conversion of a β-Ketoacyl Snythase to a Malonyl Decarboxylase by Replacement of the Active-Site Cysteine with Glutamine," *Biochemistry* 38(36):11643-11650.
Written Opinion of the International Searching Authority mailed on Jan. 23, 2006, for PCT Patent Application No. PCT/US2004/022908, filed on Jul. 16, 2004, 5 pages.
Written Opinion of the International Searching Authority mailed on Nov. 20, 2007, for PCT Application No. PCT/US2007/016774, filed Jul. 25, 2007, 6 pages.
Written Opinion of the International Searching Authority mailed on Nov. 4, 2009, for PCT Patent Application No. PCT/US2009/043725, filed on May 13, 2009, 6 pages.
Worthington-Biochem. (Date Unknown). "Proteinase K," located at <http://worthington-biochem.com/PROK.html>, last visited on Mar. 2, 2004, 4 pages.
Wu, X. (2000, e-pub. Jan. 19, 2000). "Cloning of Amadoriase I Isoenzyme from *Aspergillus* sp.: Evidence of FAD Covalently Linked to Cys342," *Biochemistry* 39(6):1515-1521.
Wu, X. et al. (2003). "Enzymatic Deglycation of Proteins," *Archives of Biochemistry and Biophysics* 419:16-24.
Xie, L.Y. et al. (1998). "Epitope Tag Mapping of the Extracellular and Cytoplasmic Domains of the Rat Parathyroid Hormone (PTH)/PTH-Related Peptide Receptor," *Endocrinology* 139(11):4563-4567.
Yoshida, N. et al. (Dec. 1995). "Distribution and Properties of Fructosyl Amino Acid Oxidase in Fungi," *Applied and Environmental Microbiology* 61(12):4487-4489.
Yoshida, N. et al. (1996). "Primary Structure of Fungal Fructosyl Amino Acids Oxidaeses and their Application to the Measurement of Glycated Proteins," *European Journal of Biochemistry* 242(3):499-505.
International Preliminary Report on Patentability issued on Nov. 17, 2010, for PCT Patent Application No. PCT/US2009/043725, filed on May 13, 2009, 8 pages.
Non-Final Office Action for U.S. Appl. No. 12/944,586, mailed Nov. 25, 2011, 17 pages.
Response to Non-Final Office Action for U.S. Appl. No. 12/944,586, filed Feb. 27, 2012, 17 pages.
Notice of Allowance for U.S. Appl. No. 12/944,586, mailed Mar. 9, 2012, 8 pages.
Notice of Allowance for U.S. Appl. No. 12/944,586, mailed Oct. 1, 2012, 5 pages.
Second Office Action (with English translation) for CN 200780023123.5, issued Oct. 19, 2012, 14 pages.
Notice of Allowance for U.S. Appl. No. 13/083,357, mailed Oct. 9, 2012, 5 pages.
Office Action for U.S. Appl. No. 13/673,932, mailed Jan. 9, 2013.
The 3rd Office Action (translation) for CN 200780023123.5, mailed Feb. 28, 2013.
Notice of Reasons for Rejection (translation) for JP 2009-521827, mailed Mar. 15, 2013.
Notice of Allowance for U.S. Appl. No. 13/673,932, mailed Jun. 6, 2013.
Response to Non-Final Office Action for U.S. Appl. No. 13/673,932, filed May 9, 2013, 11 pages.
The Fourth Office Action (including translation) for CN 200780023123.5, mailed Jun. 18, 2013, 6 pages.
The Second Office Action (including translation) for CN 200980123476.1, mailed Jul. 9, 2013, 13 pages.
Response to Office Action for CN 200980123476.1, filed Sep. 23, 2013, 3 pages.
Notice of Grant of Invention (with translation) for CN 200780023123.5, issued Aug. 20, 2013, 4 pages.

\* cited by examiner

ELECTROCHEMICAL BIOSENSOR FOR DIRECT DETERMINATION OF PERCENTAGE OF GLYCATED HEMOGLOBIN

CROSS-REFERENCE TO RELATED APPLICATIONS

This application claims the priority benefit of provisional patent application U.S. Ser. No. 61/052,888, filed May 13, 2008, which is incorporated herein in its entirety by reference.

FIELD OF THE INVENTION

The present invention relates to electrochemical biosensors for measuring the percentage of glycated hemoglobin (HbA1c) in blood samples without a separate measurement of total hemoglobin. HbA1c biosensors can be used for diabetic monitoring at doctor's offices or homes of patients.

BACKGROUND OF THE INVENTION

A glycated protein is a substance which is produced by the non-enzymatic and irreversible binding of the amino group of an amino acid constituting a protein, with the aldehyde group of a reducing sugar such as aldose. See e.g., U.S. Pat. No. 6,127,138. Such a non-enzymatic and irreversible binding reaction is also called "Amadori rearrangement," and therefore the above-mentioned glycated protein may also be called "Amadori compound" in some cases.

Nonenzymatic glycation of proteins has been implicated in the development of certain diseases, e.g., diabetic complications and the aging process (Takahashi et al., *J. Biol. Chem.*, 272(19):12505-7 (1997); and Baynes and Monnier, *Prog. Clin. Biol. Res.*, 304:1-410 (1989)). This reaction leads to dysfunction of target molecules through formation of sugar adducts and cross-links. Considerable interest has focused on the Amadori product that is the most important "early" modification during nonenzymatic glycation in vitro and in vivo.

Various assays for glycated proteins are known. For example, U.S. Pat. No. 6,127,138 discloses that a sample containing a glycated protein is treated with Protease XIV or a protease from *Aspergillus* genus, thereafter (or while treating the sample with the above protease) FAOD (fructosyl amino acid oxidase) is caused to react with the sample so as to measure the amount of oxygen consumed by the FAOD reaction or the amount of the resultant reaction product, thereby to measure the glycated protein.

In another example, U.S. Pat. No. 6,008,006 discloses that the amount of glycated proteins in a sample can be quantified by reacting the sample with first a reagent which is a combination of a protease and a peroxidase and second with a ketoamine oxidase. U.S. Pat. No. 6,008,006 also discloses a kit which contains the combined peroxidase/protease enzyme reagent and also the ketoamine oxidase. U.S. Pub. No. 2005/0014935 discloses methods and kits for measuring amount of glycated protein using a chimeric amadoriase. U.S. Pub. No. 2003/0162242 and EP 1304385 A1 also disclose methods of selectively determining glycated hemoglobin.

Methods for determining percentage of glycated hemoglobin A1c that require a separate measurement of total hemoglobin in the samples have been described. When a chemistry analyzer is used to determine the value of percentage of glycated hemoglobin A1c, a dual channel format is required. In this format, two separate assays are performed to determine 1) glycated hemoglobin A1c concentration, and 2) total hemoglobin concentration in the samples; and followed by calculating the ratio of glycated HbA1c to total hemoglobin to obtain percentage of HbA1c. Methods of directly assaying percentage of glycated hemoglobin without a separate measurement of total hemoglobin are described in WO 2008/013874.

Various electrochemical biosensors are known to use specific enzyme reactions to determine the amount of an analyte that serves as the enzyme substrate through electrochemical detection methods. The most utilized biosensor is the biosensor for glucose test that utilizes glucose oxidase to react with glucose in the blood and to generate $H_2O_2$ for detection electrochemically using designed electrodes including working, counter and reference with or without a mediator or catalyst. Electrode sensors for $H_2O_2$ detection have been well developed and electrode strips for $H_2O_2$ detection have now become commercially available. See, e.g., Luo et al., Biosensors and Bioelectronics 22:482-488, 2006; Wang et al., Chem. Rev. 108:814-825, 2008; U.S. App. Pub. No. 2009/0090623.

Besides the glucose test, an HbA1c test has become another important test for better monitoring diabetic conditions. Glucose tests report the glucose levels in the blood for the particular moment, whereas HbA1c tests give an average glucose level of the past 3 months. By testing HbA1c levels, physicians can have a better understanding on how their patients' glucose levels were controlled in the past 3 months, which in turn helps doctors to make therapeutic decisions. Recently, there is a growing trend to use HbA1c test as a screen test for identification of diabetic conditions. Therefore, a HbA1c test device that is as simple as a glucose meter and can be used by patients as a self-test device is highly desirable.

SUMMARY OF THE INVENTION

The invention provides an electrode device for use in an electrochemical sensor for measuring percentage of glycated hemoglobin (HbA1c) in a sample, comprising: an electrode support; a working electrode placed on the electrode support, wherein a fructosyl amino acid oxidase is placed (such as deposited) on or near the working electrode; and a counter or a reference electrode placed on the electrode support and spaced from the working electrode.

In some embodiments, the device further comprises a reference or a counter electrode placed on the electrode support and spaced from the other electrodes on the support.

In some embodiments, the working electrode and/or the counter electrode further comprise a mediator which shuttles electrons between the hydrogen peroxide generated from said fructosyl amino acid oxidase-catalyzed reaction and the working electrode to create a current representative of the amount of the glycated hemoglobin in the sample. The mediator may comprises one or more agents selected from the group consisting of ferrocene, Prussian Blue, metal phthalocyonine, and tetrathiafulvalene (TTF). Other mediators capable of shuttling electrons between the reaction media and the electrode may also be used.

In some embodiments, the working electrode and/or the counter electrode further comprise a catalyst which catalyzes the redox reaction of hydrogen peroxide. The catalyst comprises one or more platinum group metal such as Ir-carbon, Rh-carbon, and Ru-carbon. In some embodiments, Ir-carbon, Rh-carbon, and Ru-carbon are nanoparticles.

In some embodiments, the device may further comprise a first oxidizing agent which selectively oxidizes a low molecular weight reducing substance and/or a second oxidizing agent which selectively oxidizes a high molecular weight reducing substance which are placed (such as deposited) on or near the working electrode. For example, the first oxidizing agent and/or the second oxidizing agent may be placed on the electrode support. In some embodiments, the device may further comprise one or more proteases which digest glycated hemoglobin into glycated peptides or glycated amino acids which are placed (such as deposited) on or near the working electrode. For example, the one or more proteases may be placed on the electrode support. In some embodiments, the device may further comprise a detergent that lyses red blood cells in a blood sample and releases hemoglobin, wherein the detergent is placed (such as deposited) on or near the working electrode, or in a sample well separated from the electrodes.

In some embodiments, the fructosyl amino acid oxidase is formulated in a matrix and is placed on or near the working electrode. In some embodiments, one or more proteases which digest glycated hemoglobin into glycated peptides or glycated amino acids are formulated in a matrix and are placed on the top of the matrix containing the fructosyl amino acid oxidase on the working electrode. In some embodiments, the matrix comprises an enzyme immobilizing agent (such as a linking agent) and a thickening polymer.

In some embodiments, the device further comprises an insulation/covering layer defining an enclosed space over the working, counter and/or reference electrodes, wherein said insulation/covering layer forms a well for receiving a sample, wherein the sample well is located on the electrodes or near the electrodes. In some embodiments, the device further comprises a sample transfer path between said sample well and said working electrode. In some embodiments, the sample well contains a first oxidizing agent which selectively oxidizes a low molecular weight reducing substance and a second oxidizing agent which selectively oxidizes a high molecular weight reducing substance. In some embodiments, the sample well further contains one or more proteases which digest glycated hemoglobin into glycated peptides or glycated amino acids. In some embodiments, the sample well further contains a detergent that lyses red blood cells in a blood sample and releases hemoglobin. In some embodiments, the device comprises a capillary-fill channel for receiving a sample through capillary action, wherein one end of the channel is in contact with the working electrode.

In some embodiments, the working electrode and/or the counter electrode in the device described herein comprises a metallized carbon selected from the group consisting of Ir-carbon, Rh-carbon, and Ru-carbon. In some embodiments, the reference electrode in the device described comprises Ag/AgCl.

In some embodiments, the electrodes are screen-printed using thick film technology or using thin film lithography.

The invention also provides a method of measuring percentage of glycated hemoglobin (HbA1c) in a sample, comprising a) applying a blood sample to the working electrode of the electrode device described herein, wherein the blood sample has been treated with or is treated in the device with 1) a detergent which lyses red blood cell and releases hemoglobin from red blood cells in the blood sample; 2) a first oxidizing agent which selectively oxidizes a low molecular weight reducing substance; 3) a second oxidizing agent which selectively oxidizes a high molecular weight reducing substance, and 4) a protease which digests glycated hemoglobin into glycated peptides or glycated amino acids; b) applying an electrical potential between the working electrode and the reference electrode suitable for monitoring the hydrogen peroxide generated from the fructosyl amino acid oxidase-catalyzed reaction; c) measuring an electrical current between the working electrode and the counter electrode or a charge passed at the working electrode; and whereby the percentage of glycated hemoglobin in the sample is determined based on the measured current or charge as compared to a reference (such as a calibration curve) without measuring the total hemoglobin in the blood sample separately. The blood sample may be applied to the working electrode by pipetting the sample onto the working electrode, by dipping the electrode device into the sample, or by capillary action through a capillary-fill channel.

The invention also provides a method of measuring percentage of glycated hemoglobin (HbA1c) in a sample, comprising a) applying a blood sample to the sample receiving well of the electrode device described herein, wherein the blood sample has been treated with or is treated in the device with 1) a detergent which lyses red blood cell and releases hemoglobin from red blood cells in the blood sample; 2) a first oxidizing agent which selectively oxidizes a low molecular weight reducing substance; 3) a second oxidizing agent which selectively oxidizes a high molecular weight reducing substance, and 4) a protease which digests glycated hemoglobin into glycated peptides or glycated amino acids; b) applying an electrical potential between the working electrode and the reference electrode suitable for monitoring the hydrogen peroxide generated from the fructosyl amino acid oxidase-catalyzed reaction; c) detecting or measuring an electrical current between the working electrode and the counter electrode or a charge passed at the working electrode; and whereby the percentage of glycated hemoglobin in the sample is determined based on the measured current or charge as compared to a reference (such as a calibration curve) without measuring the total hemoglobin in the blood sample separately. In some embodiments, the blood sample is lysed in a lysing buffer in a separate tube or vial, and the blood lysate is then applied into the sample receiving well.

In any of the methods described herein, the hydrogen peroxide generated by the fructosyl amino acid oxidase-catalyzed reaction is electrochemically detected directly or indirectly via a mediator or a catalyst. In any of the methods described herein, the electrical potential is applied between the working electrode and the reference electrode in a time delayed manner.

In some embodiments, the electrode device described herein may further comprise a second working electrode and an additional enzyme that reacts with glucose such as glucose oxidase or glucose dehydrogenase to measure both HbA1c and glucose using a single device.

The invention also provides an electrochemical biosensor comprising the electrode device described herein and an apparatus (such as a reader) for signal detection. In some embodiments, the apparatus for signal detection may further comprise a wireless data connection which transfers the test results to a data base or to one or more email addresses.

The invention also provides a kit for measuring percentage of glycated hemoglobin (HbA1c) in a sample, said kit comprising an electrode device described herein, and a reader for detecting the electrical current or charge generated from the electrode device. The kit may further comprise a reagent which lyses blood cells to release hemoglobin; a first oxidizing agent which selectively oxidizes a low molecular weight reducing substance; a second oxidizing agent which selectively oxidizes a high molecular weight reducing substance; and/or a protease which digests glycated hemoglobin into glycated peptides or glycated amino acids. The kit may further comprise instruction to perform the methods described herein.

It is to be understood that one, some, or all of the properties of the various embodiments described herein may be combined to form other embodiments of the present invention. These and other aspects of the invention will become apparent to one of skill in the art.

BRIEF DESCRIPTION OF THE SEVERAL VIEWS OF THE DRAWING(S)

DETAILED DESCRIPTION OF THE INVENTION

Figure 1:
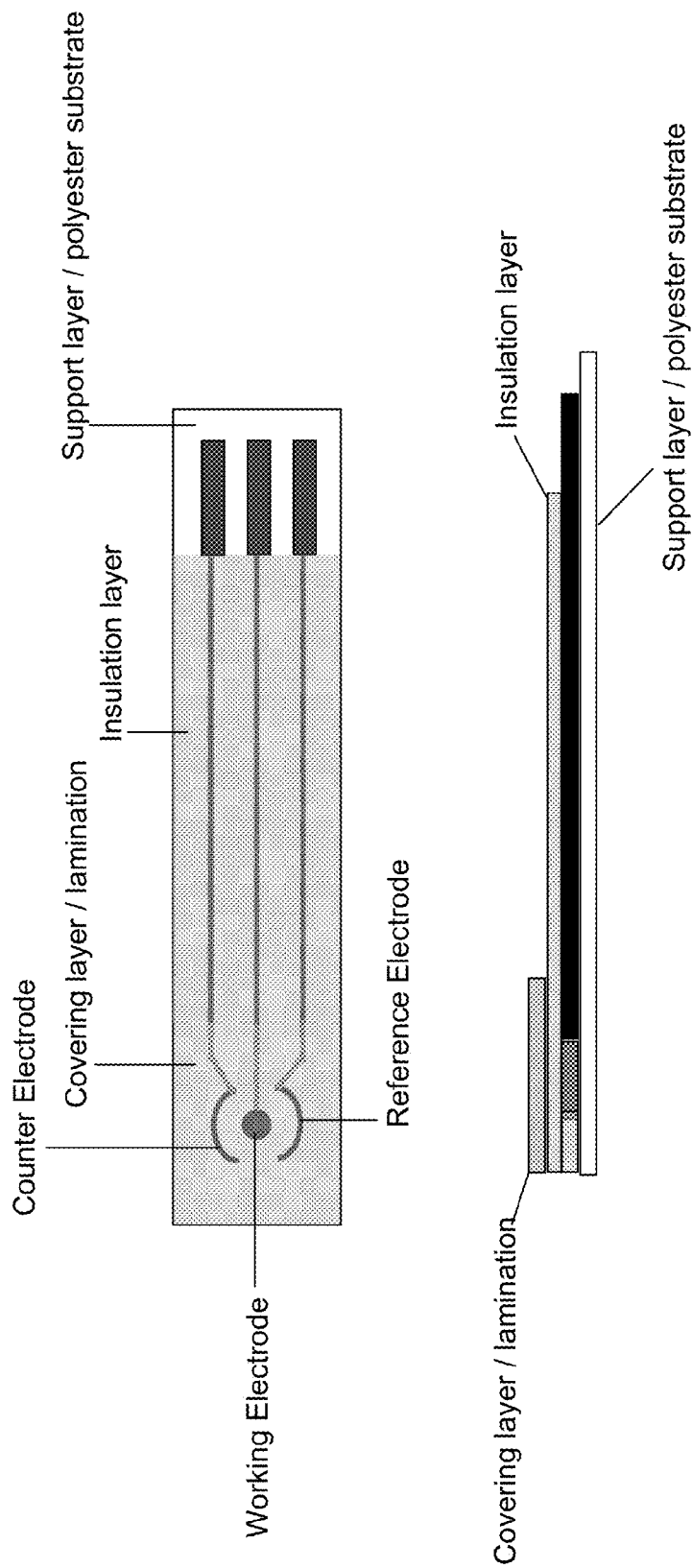
FIG. 1 shows an electrode device with three electrodes: working electrode, reference electrode, and counter electrode.
Figure 2:
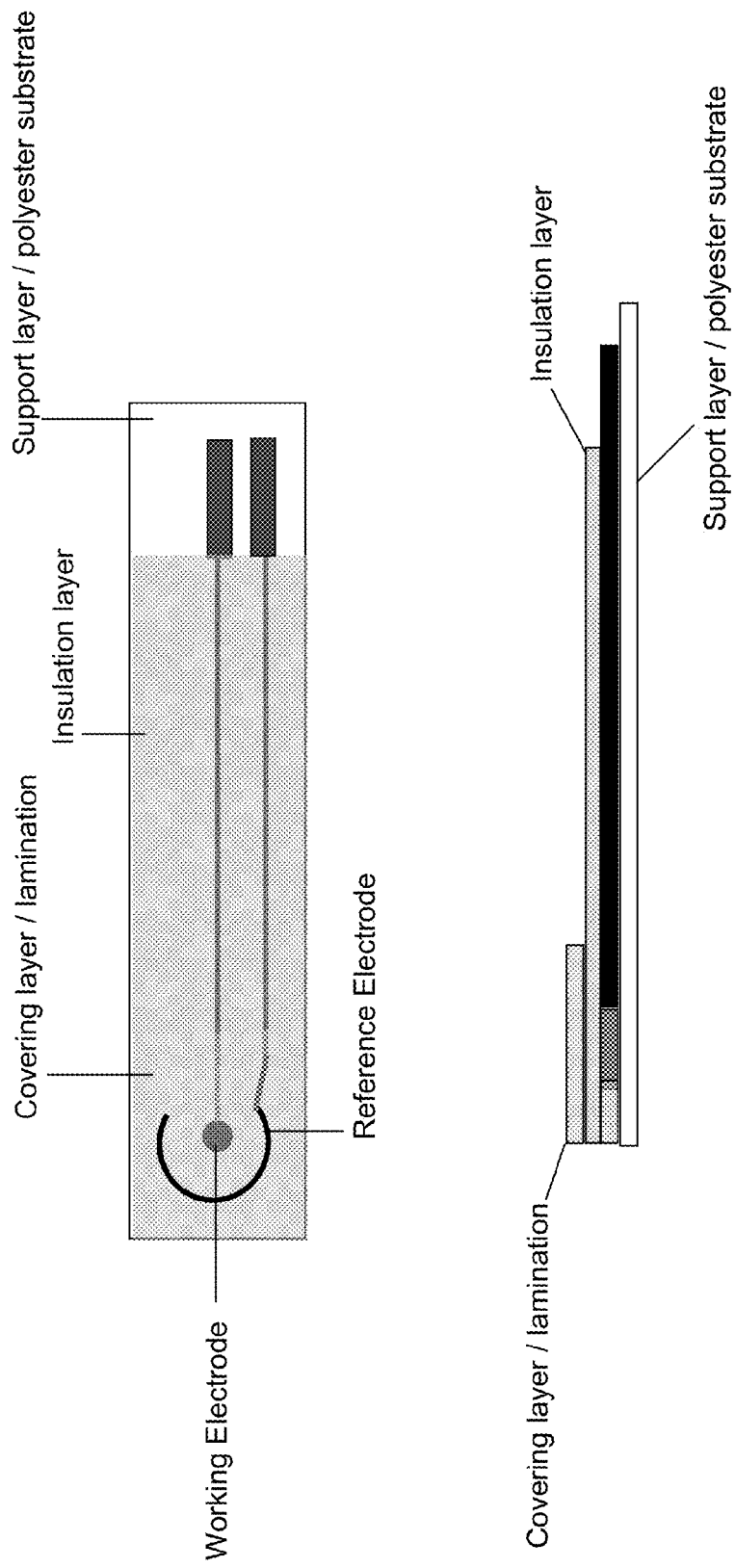
FIG. 2 shows an electrode device with two electrodes: working electrode and reference electrode.

The invention provides electrochemical biosensors for measuring the percentage of glycated hemoglobin (HbA1c) in blood samples without a separate measurement of total hemoglobin and methods of using these biosensors. The biosensors are based on the principle of enzymatic generation of $H_2O_2$ from glycated hemoglobin molecules and electrochemical detection of $H_2O_2$ using an electrochemical biosensor.

The biosensors described are designed to measure the percentage of glycated hemoglobin (HbA1c) in blood samples using methods involving the following reactions or process to generate $H_2O_2$: a) lysing red blood cells in a blood sample with a lysing buffer to release hemoglobin; b) oxidizing the lysate with a first oxidizing agent which selectively oxidizes low molecular weight reducing substances; c) oxidizing the lysate with a second oxidizing agent which selectively oxidizes high molecular weight reducing substances; d) contacting the lysate with a protease to form protein fragments and/or amino acids containing glycated peptides and/or glycated amino acids; and e) contacting the protein fragments with a fructosyl amino acid oxidase (such as fructosyl valine oxidase (FVO)) to generate hydrogen peroxide ($H_2O_2$). The $H_2O_2$ generated is measured using a biosensor, and the electrical current or charge measured from the biosensor is used to determine the percentage of total glycated hemoglobin or percentage of glycated hemoglobin A1c in the sample by comparing the measured current or charge to a reference (such as a calibration curve) without measuring the total hemoglobin in the blood sample separately. By using a reference (such as a calibration curve), HbA1c in the sample can be directly reported by using a $H_2O_2$ detection electrode device and a signal detecting meter without the need of a separate measurement of total hemoglobin.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, a "fructosyl amino acid oxidase" or "FAOD" refers to an enzyme catalyzing the oxidative deglycation of Amadori products to yield corresponding amino acids, glucosone, and $H_2O_2$, as shown in the following reaction:

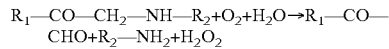

$$R_1\text{—CO—CH}_2\text{—NH—}R_2+O_2+H_2O \rightarrow R_1\text{—CO—CHO}+R_2\text{—NH}_2+H_2O_2$$

wherein $R_1$ represents the aldose residue of a reducing sugar and $R_2$ represents a residue of an amino acid, protein or peptide. An example of FAOD is fructosyl valine oxidase (FVO). Other synonyms of amadoriase includes amadoriase and fructosyl amine:oxygen oxidoreductase (FAOO). For purposes herein, the name "fructosyl amino acid oxidase" is used herein, although all such chemical synonyms are contemplated. "Fructosyl amino acid oxidase" also encompasses a functional fragment or a derivative that still substantially retain its enzymatic activity catalyzing the oxidative deglycation of Amadori products to yield corresponding amino acids, glucosone, and $H_2O_2$. Typically, a functional fragment or derivative retains at least 50% of its amadoriase activity. Preferably, a functional fragment or derivative retains at least 60%, 70%, 80%, 90%, 95%, 99% or 100% of its amadoriase activity. It is also intended that a fructosyl amino acid oxidase can include conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in nonessential regions of a polypeptide do not substantially alter biological activity (see, e.g., Watson, et al., *Molecular Biology of the Gene*, 4th Edition, 1987, The Benjamin/Cummings Pub. Co., p. 224). Such exemplary substitutions are preferably made in accordance with those set forth in TABLE 1 as follows:

TABLE 1

| Original residue | Conservative substitution |
| --- | --- |
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |

TABLE 1-continued

| Original residue | Conservative substitution |
|---|---|
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, "peroxidase" refers to an enzyme that catalyses a host of reactions in which hydrogen peroxide is a specific oxidizing agent and a wide range of substrates act as electron donors. It is intended to encompass a peroxidase with conservative amino acid substitutions that do not substantially alter its activity. The chief commercially available peroxidase is horseradish peroxidase.

As used herein, a "composition" refers to any mixture of two or more products or compounds. It may be a solution, a suspension, a liquid, a powder, a paste, aqueous, non-aqueous, or any combination thereof.

Figure 3:
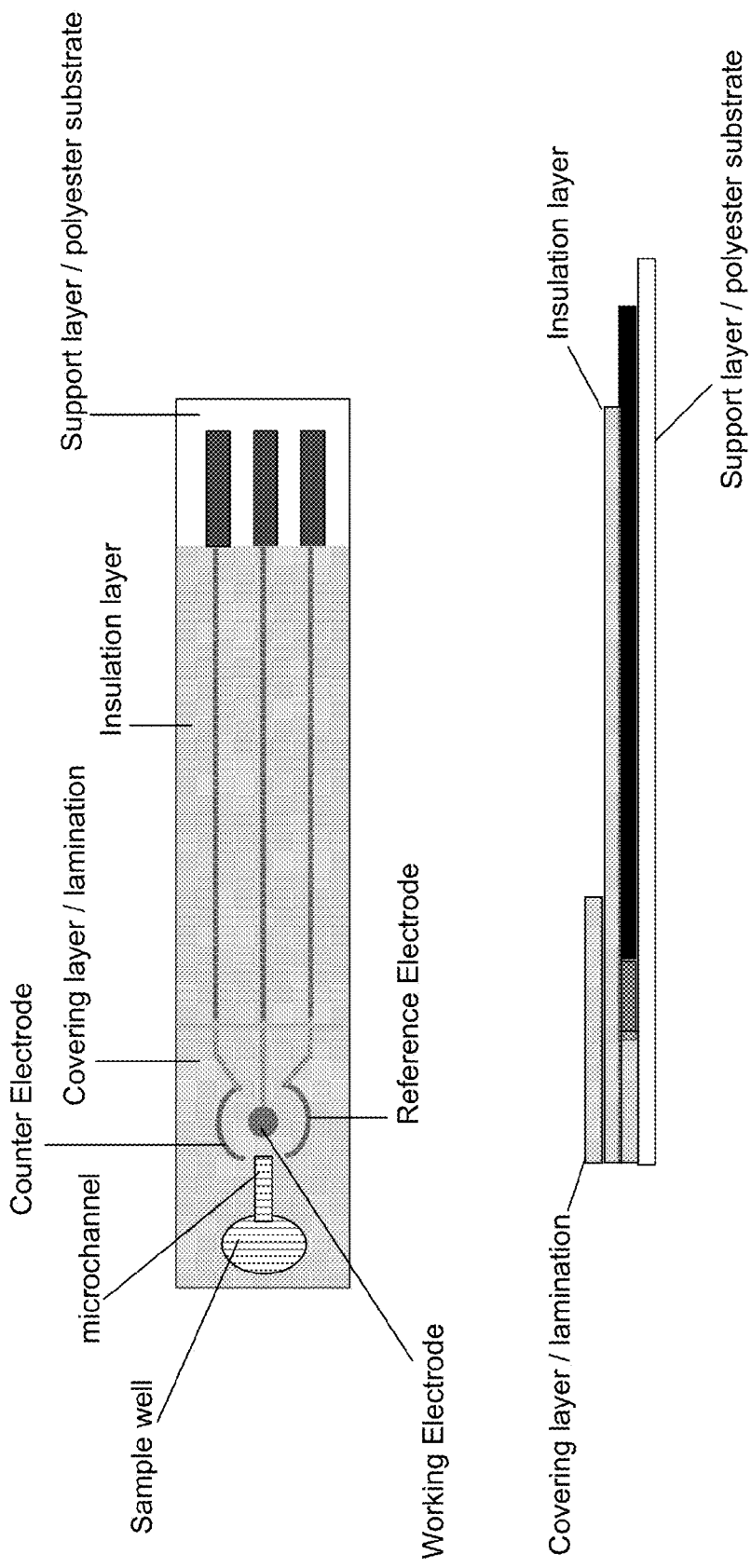
FIG. 3 shows an electrode device with three electrodes (working electrode, reference electrode, and counter electrode), a separate sample receiving well, and a microchannel between the sample receiving well and the working electrode.
Figure 4:
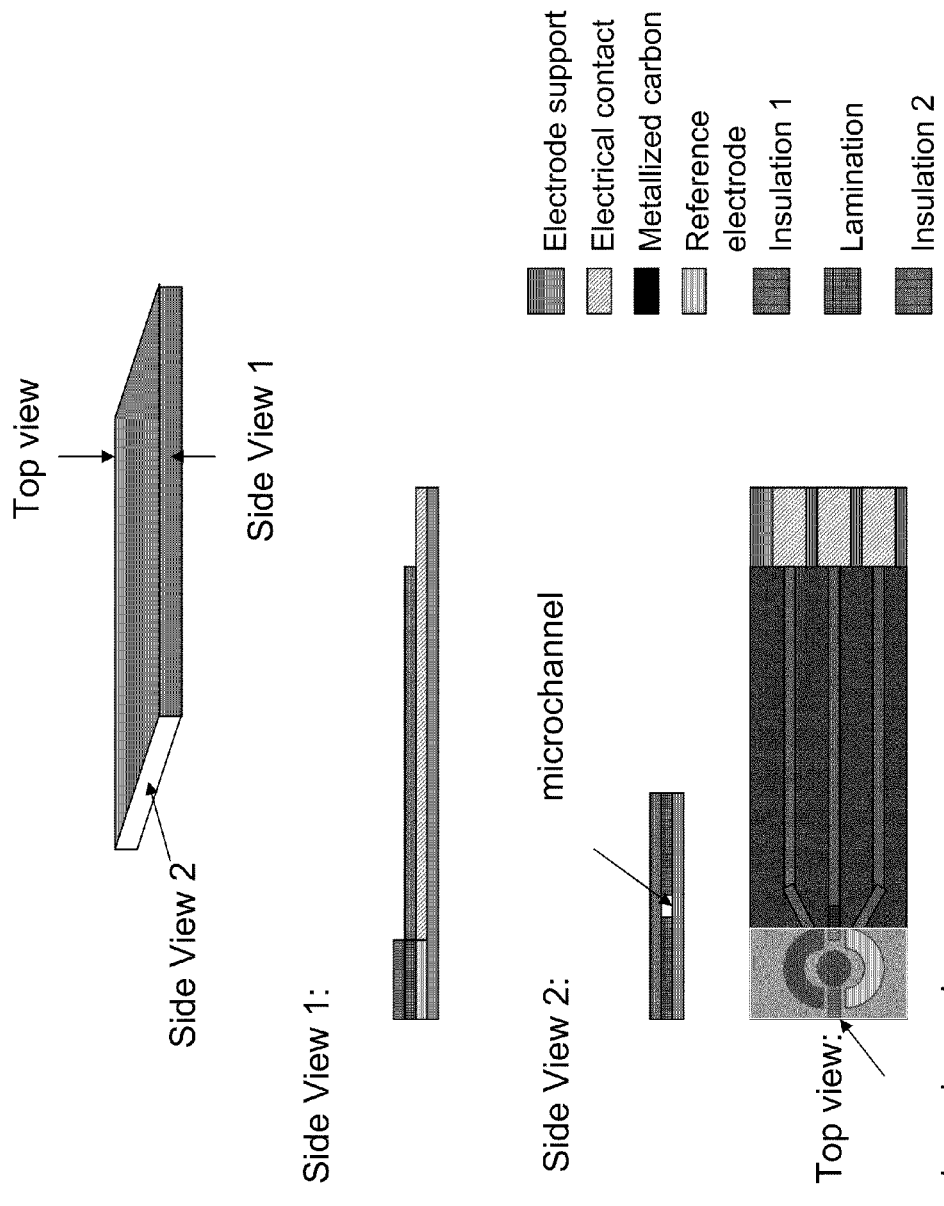
FIG. 4 shows an electrode device with a capillary-fill microchannel. The microchannel is formed by lamination on top of the electrode support.

B. Electrochemical Biosensors for Directly Assaying Percentage of Glycated Hemoglobin In one aspect, the invention provides an electrode device for use with an electrochemical detector for measuring the percentage of glycated hemoglobin (HbA1c) in a blood sample without a need of a separate measurement of the total amount of hemoglobin. The electrode device is so designed that it specifically measures the amount of $H_2O_2$ generated by a specific enzymatic reaction catalyzed by a fructosyl amino acid oxidase (such as a fructosyl valine oxidase (FVO)). The electrode device comprises an electrode support on which a working and a reference electrode, a working and a counter electrode, or a working, a reference and a counter electrode are placed. The electrodes are spaced from each other on the electrode support. The enzyme FAOD is placed (such as deposited or cast) on or near (including around) the working electrode. The electrodes may be covered by an insulation layer to protect the electric connecting pathway and to define the electrode area or electrode contacts. See FIGS. 1-4. The electrode device may further comprise a covering layer to form a sample well with a defined space. See FIG. 3. The sample well can be located around the working electrode or in a separate position which is connected to the working electrode through a sample transfer path (such as a microchannel). See FIG. 3. The sample well may also be in the form of a capillary-fill channel which allows the sample receiving through capillary action. One end of the capillary-fill channel is in contact with the working electrode. The capillary-fill channel can be created by a layer through lamination. An example of such capillary-fill channel is shown in FIG. 4. Any other sample well or capillary-fill channel design known in the art may be included in the device. See, e.g., U.S. Pat. No. 6,270,637.

An electrochemical biosensor generally includes an electrode device and an apparatus (reader) for signal detection. The apparatus for signal detection may further comprise a wireless data connection which transfers the test results to a data base or to one or more email addresses.

The electrodes may be made by any methods known in the art. For example, electrodes may be made by thick-film technology (such as screen-printing and ink-jet printing) or thin film lithography on the electrode support (such as a polyester substrate). In some embodiments, the electrical contacts of the electrodes are silver, and electrodes (working, counter and/or reference) are printed on the top of silver electrode bases. In some embodiments, the working electrode and/or the counter electrode are screen-printed with metallized carbons such as Ir-Carbon, Rh-Carbon, and Ru-Carbon. In some embodiments, Ir-Carbon, Rh-Carbon, and Ru-Carbon are nanoparticles. In some embodiments, the reference electrode is screen-printed with Ag/AgCl.

In some embodiments, a catalyst such as platinum group metal (Rh, Ir, Ru, Os) is included in the working electrode and/or the counter electrode. For example, the catalyst can be deposited by combining into a conductive composition for printing the electrode. The conductive composition includes, but is not limited to, a metallized carbon, a polymer (comprising a binder and a water-strength polymer) and water or an inorganic solvent (such as 0.1 M, pH 7.0 phosphate buffer). The metal in the metallized carbon can be pure metal such as platinum, gold, silver, palladium, ruthenium, rhodium, iridium, oxide or alloys thereof. For example, the metallized carbon includes metal coated on the surface of the carbon particle with nano-sized dimension. The binder includes hydroxyethyl cellulose or hydroxypropyl cellulose. The wet-strength polymer includes polyethylenimine; poly(acrylic acid), potassium salt; poly(acrylic acid), sodium salt; poly (acrylic acid-co-acrylamide), potassium salt; poly(acrylic acid), sodium salt-graft-poly(ethylene oxide); poly(2-hydroxyethyl methacrylate); poly(2-hydroxypropyl methacrylate); poly(isobutylene-co-maleic acid) or combinations thereof. Generally, the binder is cross-linked with the wet-strength polymer. Therefore, after forming the electrode on the strip by screen printing, the water or inorganic solvent is evaporated by the following-up steps.

In some embodiments, a mediator is included in the working electrode and/or counter electrode, and the mediator can be selected from commonly used mediators such as ferrocene, Prussian Blue, and any other known mediators. See, e.g., U.S. Pat. Nos. 6,863,800; and 6,329,161.

In some embodiments, the electrode device comprises a strip having a substrate as the electrode support; at least two electrodes disposed on the substrate to define a sample area; and a reagent disposed on the sample area, wherein the electrode having metal in the range of 0.1-5% in weight, graphite in the range of below 55% in weight, and polymer. In some embodiments, the graphite is fine particle size and the metal is coated on the surface of the graphite particle with nano-sized dimension. The metal may comprise platinum, gold, silver, palladium, ruthenium, rhodium, iridium, oxides or alloys thereof. The polymer may comprise a binder (including hydroxyethyl cellulose or hydroxypropyl cellulose) and a wet-strength polymer (including polyethylenimine; poly (acrylic acid), potassium salt; poly(acrylic acid), sodium salt; poly(acrylic acid-co-acrylamide), potassium salt; poly (acrylic acid), sodium salt-graft-poly(ethylene oxide); poly (2-hydroxyethyl methacrylate); poly(2-hydroxypropyl methacrylate); poly(isobutylene-co-maleic acid) or combinations thereof). The electrode device may further comprise a conductive layer disposed between the electrode and the substrate; and the conductive layer may be screen-printed by graphite dispersed in an organic solvent. In some embodiments, the conductive layer and the electrode are formed by screen printing in different steps. In some embodiments, the reagent comprises an enzyme (such as a fructosyl amino acid oxidase). Examples of the electrode devices are described in U.S. Patent Application Pub. No. 2009/0090623, which is incorporated by reference in its entirety.

In some embodiments, the enzyme fructosyl amino acid oxidase (such as FVO) is formulated in a matrix containing enzyme immobilizing agent such as glutaraldehyde and thickening polymer such as 2-hydroxyethyl cellulose, and is deposited or cast near or on the working electrode. In some embodiments, the enzyme fructosyl amino acid oxidase (such as FVO) is further included in a separate reagent layer which is placed on the top of the layer of immobilized enzyme on the working electrode.

The reactions involved in measuring the percentage of glycated hemoglobin (HbA1c) use a lysing buffer which releases hemoglobin from red blood cells in the blood sample, a first oxidizing agent which selectively oxidizes a low molecular weight reducing substance, a second oxidizing agent which selectively oxidizes a high molecular weight reducing substance, and a protease which digests glycated hemoglobin into glycated peptides or glycated amino acids. One or more of these reagents may be placed (such as deposited or cast) near or on the working electrode. In some embodiments, a protease is formulated in a matrix containing enzyme immobilizing agent and thickening polymer, and is deposited or cast near or on the working electrode. In some embodiments, the protease(s) is further included in a separate reagent layer which is placed on the top of the layer of immobilized FAOD enzyme near or on the working electrode. In some embodiments, the electrode device may further comprise a sample well, a sample transfer path (such as microchannel) from the sample well to the working electrode, or a capillary-fill channel, and one or more of the reagents may be placed (such as deposited or cast) in the sample well, the sample transfer path or the capillary-fill channel. For example, the hemoglobin in the blood sample is digested into glycated peptides or glycated amino acids before reaching the working electrode. In some embodiments, one or more of these reagents are placed (such as deposited or cast) on the strip support in the area surrounding the working electrode or in the area between the counter electrode and the working electrode and/or between the reference electrode and the working electrode. For example, these reagents may be mixed with ink based solution and screen-printed on the strip support.

In a further embodiment, the electrode device is configured as a biopotentiostats that contains two working electrodes, one counter electrode and one reference electrode. One working electrode is used for HbA1c test and the other is used for glucose test. The enzyme used for glucose test can be glucose oxidase or glucose dehydrogenase, and the enzyme used for HbA1c test is the fructosyl amino acid oxidase (such as FVO).

The electrode device of the invention can be in different electrode structures and can be made using methods known in the art. For example, electrode device may be made with screen-printing methods. See, e.g., U.S. Pat. Nos. 5,682,884; 5,120,420; 5,320,732.

Blood samples that can be assayed using the electrode device include whole blood or collected blood cells. The red blood cells in the blood sample are lysed to release hemoglobin. Any lysing buffer (e.g., in the acidic or alkaline pH ranges) that can lyse the red blood cells and release the hemoglobin can be used. Lysing buffer generally contains a detergent, such as Triton (e.g., Triton X-100), Tween (e.g., Tween 20), sodium dodecyl sulfate (SDS), cetyltrimethylammonium bromide (CTAB), tetradecyltrimethylammonium bromide (TTAB), polyoxyethylene lauryl ethers (POEs), and Nonidet P-40 (NP-40).

Any suitable protease can be used. Either an endo-type protease or an exo-type protease can be used. Exemplary endo-type proteases include trypsin, α-chymotrypsin, subtilisin, proteinase K, papain, cathepsin B, pepsin, thermolysin, protease XVII, protease XXI, lysyl-endopeptidase, prolether and bromelain F. Exemplary exo-type proteases include an aminopeptidase or a carboxypeptidase. In one example, the protease is proteinase K, pronase E, ananine, thermolysin, subtilisin or cow pancreas proteases. Metaloproteases and neutral proteinases from *Aspergillus* sps, *Alicyclobacillus* sps, and *Bacillus* sps may also be used.

The protease can be used to generate a glycated peptide of any suitable size. For example, the protease can be used to generate a glycated peptide from about 2 to about 30 amino acid residues. In another example, the protease is used to generate glycated glycine, glycated valine or glycated lysine residue or a glycated peptide comprising glycated glycine, glycated valine or glycated lysine residue.

Glycated peptide and/or glycated amino acid are contacted with a fructosyl amino acid oxidase. Any fructosyl amino acid oxidase (FAOD) can be used. Fructosyl amino acid oxidase may be purified or recombinantly produced. Any naturally occurring species may be used. In one example, the FAOD used is of *Aspergillus* sp. origin (See, e.g., Takahashi et al., *J. Biol. Chem.* 272(6):3437-43, 1997). Other fructosyl amino acid oxidase, e.g., disclosed in GenBank Accession No. U82830 (Takahashi et al., *J. Biol. Chem.*, 272(19):12505-12507 (1997) and disclosed U.S. Pat. No. 6,127,138 can also be used. A functional fragment or a derivative of an amadoriase that still substantially retain its enzymatic activity catalyzing the oxidative deglycation of Amadori products to yield corresponding amino acids, glucosone, and $H_2O_2$ can also be used.

Normally, a functional fragment or a derivative of an amadoriase retains at least 50% of its enzymatic activity. Preferably, a functional fragment or a derivative of an amadoriase retain at least 50%, 60%, 70%, 80%, 90%, 95%, 99% or 100% of its enzymatic activity.

Any of the chimeric proteins having the enzymatic activities of FVO described in the U.S. Pub. No. 2005/0014935 can be used. In some embodiments, the fructosyl amino acid oxidase comprises from the N-terminus to C-terminus: a) a first peptidyl fragment comprising a bacterial leader sequence from about 5 to about 30 amino acid residues; and b) a second peptidyl fragment comprising an FVO. In some embodiments, the FVO comprises the following amino acid sequence:

```
                                         (SEQ ID NO: 1)
MGGSGDDDDLALAVTKSSSLLIVGAGTWGTSTALHLARRGYTNVTVLDPY

PVPSAISAGNDVNKVISSGQYSNNKDEIEVNEILAEEAFNGWKNDPLFKP

YYHDTGLLMSACSQEGLDRLGVRVRPGEDPNLVELTRPEQFRKLAPEGVL

QGDFPGWKGYFARSGAGWAHARNALVAAAREAQRMGVKFVTGTPQGRVVT

LIFENNDVKGAVTGDGKIWRAERTFLCAGASAGQFLDFKNQLRPTAWTLV

HIALKPEERALYKNIPVIFNIERGFFFEPDEERGEIKICDEHPGYTNMVQ

SADGTMMSIPFEKTQIPKEAETRVRALLKETMPQLADRPFSFARICWCAD

TANREFLIDRHPQYHSLVLGCGASGRGFKYLPSIGNLIVDAMEGKVPQKI

HELIKWNPDIAANRNWRDTLGRFGGPNRVMDFHDVKEWTNVQYRDISKLK

GELEGLPIPNPLLRTGHHHHHH.
```

The chimeric protein may be produced in bacterial cells, such as *E. coli*. The protein produced may be purified and assayed for the enzymatic activities. Assays for enzymatic activities of FAOD are known in the art (See e.g., Takahashi et al., *J. Biol. Chem.*, 272(6):3437-43 (1997) and U.S. Pat. No.

6,127,138). Four exemplary assays for enzymatic activities of amadoriases are disclosed in Takahashi et al., *J. Biol. Chem.,* 272(6):3437-43 (1997).

The first oxidizing agent is a type of oxidizing agent that selectively oxidizes low molecular weight (M.W.<3000) reducing substances. The first oxidizing agent has higher oxidizing power toward low molecular weight reducing substances than high molecular weight (M.W.>3000) reducing substances. Examples of low molecular weight substances in the blood sample are ascorbic acid and free thio containing molecules. Examples of first oxidizing agent are Dess-Martin periodinane and N-ethyl maleimide. Other examples of first oxidizing agents are sodium iodoacetate, sodium periodate, and Chloramine-T. In some embodiments, more than one first oxidizing agents (e.g., both Dess-Martin periodinane and N-ethyl maleimide) are used.

The second oxidizing agent is a type of oxidizing agent that selectively oxidizes high molecular weight (M.W.>3000) reducing substances. The second oxidizing agent has higher oxidizing power toward high molecular weight reducing substances than low molecular weight reducing substance. An example of high molecular weight substances in the blood sample is hemoglobin. An example of second oxidizing agent is a tetrazolium salt (e.g., 2-(4-iodophenyl)-3-(2,4-dinitrophenyl)-5-(2,4-disulfophenyl)-2H-tetrazolium monosodium salt, or 2-(4-iodophenyl)-3-(4-nitrophenyl)-5-(2,4-disulfophenyl)-2H-tetrazolium monosodium salt). Other examples of second oxidizing agent are sodium dodecyl sulfate, potassium ferricyanide (III), and potassium iodate. In some embodiments, more than one second oxidizing agent is used.

For the embodiments that a detergent, a first oxidizing agent, a second oxidizing agent and a protease are not placed in the electrode device, a blood sample may be treated with a lysing buffer, a first oxidizing agent, a second oxidizing agent and a protease before applying the sample to the electrode device. The detergent, first oxidizing agent, second oxidizing agent and protease may be formulated in one or more reagents, and may be in liquid or lyophilized powder. These reagents may be included in the kit described herein. In some embodiments, the lysing buffer and the first oxidizing agent (e.g., N-ethylmaleimide and/or Dess Martin Periodinane) may be formulated in one reagent. In some embodiments, the second oxidizing agent and the protease may be in one or separate reagent. A lysis buffer containing a detergent, Dess-Martin Periodinane and N-ethyl Maleimide may be used to lyse the blood cells. For example, a lysis buffer may contain 25-100 mM CHES pH 9.4, 1-3% Triton X-100, 0.1-5 mM (such as about any of 0.1, 0.5, 1, 2, 3, 4, or 5 mM) Dess-Martin Periodinane, and 0.2-5 mM (such as about any of 0.2, 1, 1.5, 2, 2.5, 3, 3.5, 4, 4.5, or 5 mM) N-ethyl Maleimide. Reagent R1a containing a buffer, $CaCl_2$ and a protease, and Reagent R1b containing a buffer, sodium chloride and WST3 and a protease may be mixed for use in digesting glycated hemoglobin into glycated peptide or glycated amino acids in the lysed blood sample. For example, Reagent R1a may contain 10-50 mM MES buffer pH 6.5, 5-10 mM $CaCl_2$, and 500-1500 U/ml neutral protease (Toyobo Co., Ltd.); and Reagent R1b may contain 10-50 mM MES pH 6.5, 100-200 mM sodium chloride, and 0.2-6 mM (such as about any of 0.2, 0.5, 1, 2, 3, 4, 5, or 6 mM) WST3 (2-(4-Iodopenyl)-3-(2,4-dinitrophenyl)-5-(2,4-disulfophenyl)-2H-tetrazolium, monosodium salt (manufactured by Dojindo Laboratories)), and 10-200 unit (such as about any of 10, 50, 60, 70, 80, 90, 100, 150, or 200 unit) of protease in 100 uL pH 7.0 5 mM MES buffer solution Examples of reagents are described in Example 1 herein and in U.S. Patent Application Pub. No. 2008/0096230.

The invention also provides kits comprising the electrode device described herein. The kits may further comprise reagents for use of the electrode device if not all reagents needed are placed in the electrode device. The kits may further comprise instructions for using the electrode device and/or reagents. In some embodiments, the kits comprise a electrode device described herein, a meter or a reader for detecting or measuring an electrical current between the working electrode and counter electrode or a charge passed at the working electrode of the electrode device, and one or more of the reagents selected from the group consisting of 1) a detergent which lyses red blood cell and releases hemoglobin from red blood cells in the blood sample; 2) a first oxidizing agent which selectively oxidizes a low molecular weight reducing substance; 3) a second oxidizing agent which selectively oxidizes a high molecular weight reducing substance, and 4) a protease which digests glycated hemoglobin into glycated peptides or glycated amino acids. In some embodiments, the meter or the reader comprises a lot enabling the electrode device to insert therein.

Exemplary Embodiments

FIG. 1 shows an exemplary electrode device made with screen-printing methods. This biosensor comprises a working electrode, a reference electrode, and a counter electrode. Both working electrode and counter electrode are Ir-Carbon modified or Prussian Blue modified; and the reference electrode is a Ag/AgCl electrode. These electrodes are screen-printed on a polyester substrate.

The working electrode and the counter electrode are prepared by screen-printing on the polyester substrate. The electrical contacts of these electrodes are silver, and the electrodes are first printed with a silver ink. Ir-Carbon ink or Prussian Blue ink is further printed on the silver based electrodes. Ir-Carbon ink is prepared by mixing and homogenization (for example, for about 5.0 minutes) of 0.5-2.0 g Ir-Carbon with 5-30 ml of an ink based solution containing 0.5-5 ml polyethylenimine and 0.1-1.0 g 2-hydroxyethyl cellulose. For example, Ir-Carbon ink is prepared by mixing 0.9 g Ir-Carbon with 5 ml of an ink based solution (prepared by mixing 10 ml pH 7.0 phosphate buffer with 1.36 ml polyethylenimine and 0.34 g 2-hydroxyethyl cellulose until a clear homogeneous solution has been obtained). Prussian Blue ink is prepared by mixing and homogenization (for about 5 minutes) of 0.5-2.0 g Prussian Blue particles with 5-30 ml of commercial carbon ink. The Prussian Blue particles were prepared using the following procedure. One gram of graphite powder and 10 ml 0.1 M iron (III) chloride were mixed with stirring for 2 minutes. Next, 2-20 ml of 0.1 M potassium ferricyanide were added, and the resulting solution was stirred for 10 min. The resulting mixture was filtered, and was dried at 100° C. for 2-20 hours. AgCl/Ag reference electrode is also prepared by screen-printing on the polyester substrate. The electrical contacts of the reference electrode are silver prepared by printing with a silver ink. A AgCl thick film is used and printed over the silver based electrode, serving as the Ag/AgCl reference electrode. See Fang et al., *Sensors and Actuators B* 129:818-825, 2008.

The iridium-modified electrochemical sensor structure described above is used as the basis for the construction of a fructosyl amino acid oxidase biosensor. Fructosyl amino acid oxidase (such as FVO) ink is prepared by mixing 1 ml of Ir-Carbon ink with fructosyl amino acid oxidase until a clear solution is obtained. A protease, a lysing buffer, a first oxidizing agent, and/or a second oxidizing agent described herein may also be included in the FAOD ink. The FAOD ink is added onto the Ir-Carbon working electrode and allowed to dry.

The Prussian Blue-modified electrochemical sensor structure described above may also be used as the basis for the construction of a fructosyl amino acid oxidase biosensor. Fructosyl amino acid oxidase (such as FVO) is prepared by mixing 1 ml of Prussian Blue ink with fructosyl amino acid oxidase until a clear solution is obtained. A protease, a lysing buffer, a first oxidizing agent, and/or a second oxidizing agent described herein may also be included in the FAOD ink. The FAOD ink is added onto the Ir-Carbon working electrode and allowed to dry.

C. Methods of Using Electrochemical Biosensors for Assaying Percentage of Glycated Hemoglobin The invention also provides methods of measuring percentage of glycated hemoglobin (HbA1c) in a blood sample using the electrode device described herein. If a lysing buffer containing a detergent, a first oxidizing agent, a second oxidizing agent and a protease are included in the electrode device, a blood sample may be applied directly into the electrode device. If one or more of these reagents are not included in the electrode device, a blood sample may be pretreated before applying into the electrode device. For example, a blood sample may be treated with a buffer containing a detergent, a first and a second oxidizing agent, and one or more protease(s) to lyse the blood cells in a tube. The lysate is then applied to the working electrode by pipetting onto the working electrode, by capillary-filling into the working electrode, or by dipping the electrode device into the lysed sample. If the electrode device has a sample receiving space, the lysate is applied to the sample receiving space on the electrode device for further reaction with FAOD to generate $H_2O_2$ for amperometric detection.

An electrical potential is applied between the working electrode and the counter electrode and/or between the working electrode and the reference electrode. An electrical current is measured between the working electrode and the counter electrode, between the working electrode and the reference electrode, or a charge passed at the working electrode is measured, and the measured current or charge corresponds to the amount of $H_2O_2$ generated. In some embodiments, the charge passing through the working electrode is measure over a period of time, such as 1-5 minutes.

In some embodiments, the methods of the invention comprises a) applying a blood sample to the working electrode of the electrode device, wherein the blood sample has been treated with 1) a lysing buffer which releases hemoglobin from red blood cells in the blood sample; 2) a first oxidizing agent which selectively oxidizes a low molecular weight reducing substance; 3) a second oxidizing agent which selectively oxidizes a high molecular weight reducing substance, and 4) a protease which digests glycated hemoglobin into glycated peptides or glycated amino acids; b) applying an electrical potential between said working electrode and said reference electrode (e.g., amperometrically or voltammetrically) suitable for monitoring the hydrogen peroxide generated from the fructosyl amino acid oxidase-catalyzed reaction; and c) detecting an electrical current between the working electrode and the counter electrode or a charge passed at the working electrode; and whereby the percentage of glycated hemoglobin in the sample is determined based on the measured current or charge as compared to a reference (such as a calibration curve) without measuring the total hemoglobin in the blood sample separately.

In some embodiments, the methods comprises applying a sample to a sample receiving space (e.g., an aperture, a sample well, a capillary-fill channel) of an electrode device, wherein the electrode device comprises 1) a lysing buffer which releases hemoglobin from red blood cells in the blood sample; 2) a first oxidizing agent which selectively oxidizes a low molecular weight reducing substance; 3) a second oxidizing agent which selectively oxidizes a high molecular weight reducing substance, and 4) a protease which digests glycated hemoglobin into glycated peptides or glycated amino acids; applying an electrical potential between the working electrode and the counter electrode or between the working electrode and the reference electrode (e.g., amperometrially or voltammetrically); and measuring an electrical current between the working electrode and the counter electrode or a charge passed at the working electrode; whereby the percentage of glycated hemoglobin (HbA1c) is determined based on the measured current or charge as compared to a reference (such as a calibration curve) without measuring the total hemoglobin in the blood sample separately. In some embodiments, the application of an electrical potential onto the working/reference or working/counter electrode is delayed for certain period of time to allow the reactions between the oxidants and reducing substances (such as hemoglobin) in the sample to reach completion or close to completion.

The percentage of total glycated hemoglobin or percentage of glycated hemoglobin A1c in a blood sample is determined by comparing the measured electrical current or charge to a reference (such as a calibration curve). The calibration curve is established using calibrator, i.e., samples (including blood samples and artificial calibrators) with known percentage of glycated hemoglobin or known percentage of glycated hemoglobin A1c.

In some embodiments, the calibration curve is prepared by measuring the electrical current using the biosensor for calibration samples by performing the same steps as the unknown samples without measuring the total hemoglobin separately; and graphing the correlation between the electrical current or charge of the calibration samples and the known percentage of glycated hemoglobin or known percentage of glycated hemoglobin A1c of the calibration samples. For example, whole blood samples having percentages of glycated hemoglobin A1c value assigned by comparison to a suitable higher order reference material can be used as calibrators. Alternative, the percentage of glycated hemoglobin A1c may be determined by another recognized method such as HPLC. Calibrators are tested the same way as the unknown samples using the methods described herein. The electrical current or charge measured for calibrators are plotted against the expected HbA1c value to establish the calibration curve. The calibration curve information for each lot of device may be electronically stored in the device so that there is no need for users to construct a calibration curve by themselves.

Calibrators other than whole blood sample may also be used to establish a calibration curve. Hemolysate samples (lysed blood samples), glycated peptides, glycated amino acid, and glycated amino acid derivatives in a suitable buffered protein matrix solution having percentage of glycated hemoglobin A1c value assigned by comparison to a suitable higher order reference material can be used as artificial calibrators. For example, calibration samples may be prepared in a phosphate buffered solution with 10% BSA and appropriate amounts of synthesized fructosyl propylamine (glycated amino acid) corresponding to various percentage of HbA1c (e.g., from 5% o 12%). Artificial calibrators are tested the same way as unknown samples except that the lysing step may not be used. The electrical current values measured for these calibrators are plotted against the expected HbA1c value to establish the calibration curve. Artificial calibrators may be lyophilized or stabilized for extended shelf life.

Blood samples that can be assayed using the present methods and biosensors include whole blood or collected blood cells. The present methods and biosensors may be used for any suitable purpose, such as in the prognosis or diagnosis of a disease or disorder (e.g., diabetes).

EXAMPLES

Example 1

Electrochemical Sensing of HbA1c by Pipetting a Sample onto a Biosensor or Dipping Biosensor into a Sample A biosensor with a working electrode, a reference electrode, and a counter electrode was prepared. Both working electrode and counter electrode are Ir-Carbon modified; and the reference electrode is Ag/AgCl electrode. The working electrode and the counter electrode were prepared by screen-printing on the polyester substrate. The electrical contacts of these electrodes are silver, and the electrodes were first printed with a silver ink. Ir-Carbon ink was further printed on the silver based electrodes. Ir-Carbon ink was prepared by mixing and homogenization of 0.5-2 g Ir-Carbon with 5-30 ml of an ink based solution (containing polyethylenimine and 2-hydroxyethyl cellulose). The working electrode also contains a fructosyl amino acid oxidase. Fructosyl amino acid oxidase (such as FVO having the amino acid sequence shown in SEQ ID NO:1) ink was prepared by mixing 1 ml of Ir-Carbon ink with fructosyl amino acid oxidase until a clear solution was obtained.

Ag/AgCl reference electrode was also prepared by screen-printing on the polyester substrate. The electrical contacts of the reference electrode were prepared by printing with a silver ink. A AgCl thick film was used and printed over the silver based electrode, serving as the Ag/AgCl reference electrode.

To test the biosensor, blood samples with known HbA1c percentage were lysed by a lysis buffer (50 mM CHES pH 9.4 and 2% Triton X-100) at room temperature for 10 minutes. The blood lysates were treated with oxidizing agents and protease (Toyobo Co., Ltd.) at 37° C. for 10 minutes. For example, 100 ul blood sample was lysed in 900 ul of lysis buffer containing 50 mM CHES pH 9.4, 2% Triton X-100, 0.1-5 mM (such as 0.1, 0.5, 1, 2, 3, 4, or 5 mM) Dess-Martin Periodinane, and 0.2-5 mM (such as 0.2, 1, 1.5, 2, 2.5, 3, 3.5, 4, 4.5, or 5 mM) N-ethyl Maleimide. The lysate was mixed with lyophilized powder from 5 ml reagent R1a (25 mM MES buffer pH 6.5, 5 mM $CaCl_2$, and 1000 U/ml neutral protease (Toyobo Co., Ltd.)), lyophilized powder from 2.5 mL reagent R1b (25 mM MES pH 6.5, 150 mM sodium chloride, and 0.2-6 mM (such as 0.2, 0.5, 1, 2, 3, 4, 5, or 6 mM) WST3 (2-(4-Iodopenyl)-3-(2,4-dinitrophenyl)-5-(2,4-disulfophenyl)-2H-tetrazolium, monosodium salt (manufactured by Dojindo Laboratories)), and 10-200 unit (such as 10, 50, 60, 70, 80, 90, 100, 150, or 200 unit) of protease in 100 uL pH 7.0 5 mM MES buffer solution. The final solution had a total volume of 1.1 mL and was incubated at temperature 37° C. for 10 minutes.

Figure 5:
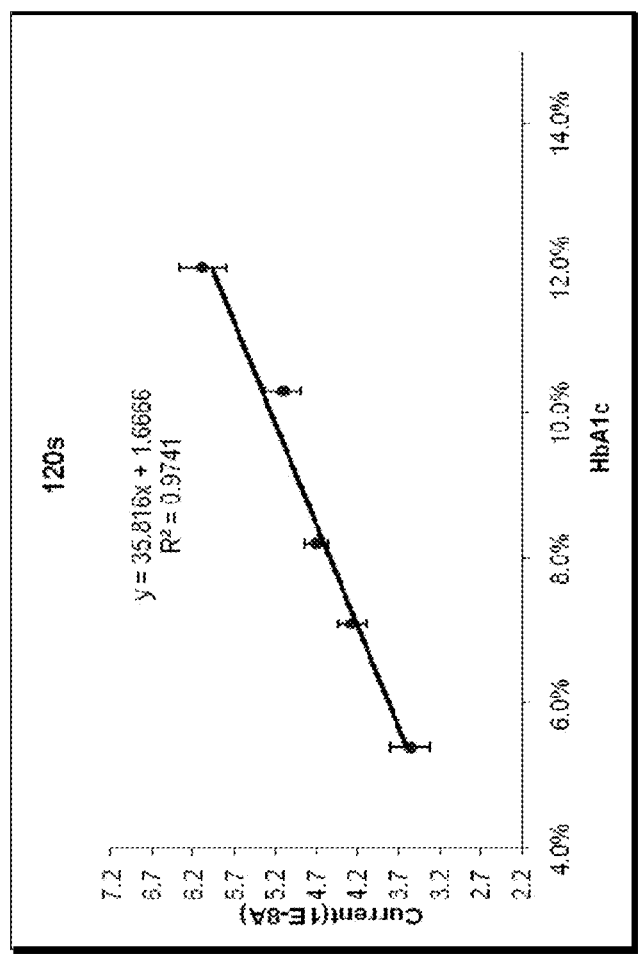
FIG. 5 shows amperometry of blood samples with known HbA1c percentages. The lysed samples were pipetted onto the biosensor for electrochemical measurement.
Figure 6:
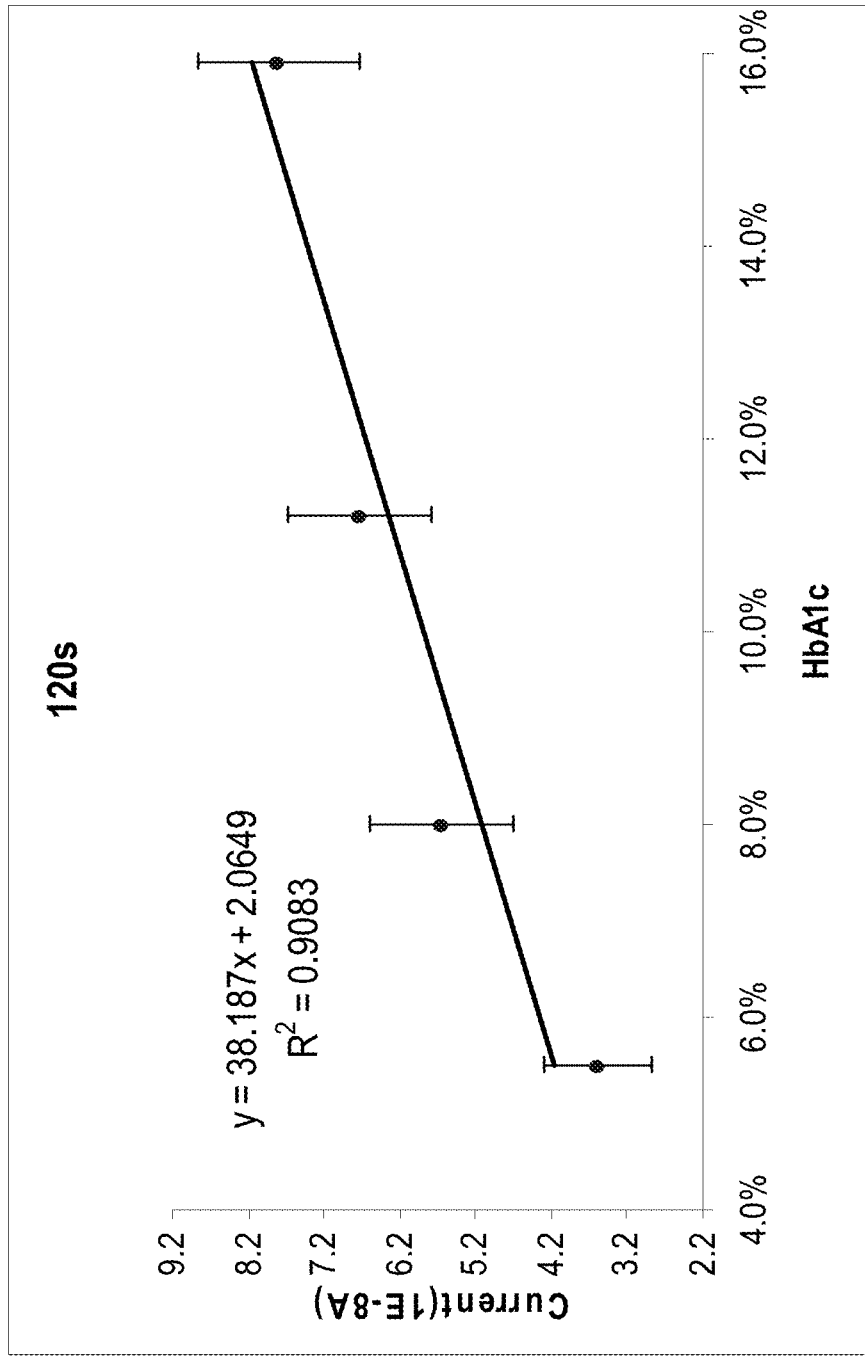
FIG. 6 shows amperometry of blood samples with known HbA1c percentages. The biosensor was dipped into the lysed blood samples for electrochemical measurement.

3 uL of the incubated solution was placed (by pipetting) onto the working electrode with enzyme FAOD for electrochemical measurement. The electrochemical measurement was carried out at +0.25V vs. the Ag/AgCl reference electrode for 120 seconds. The current between the working electrode and the counter electrode measured for each sample is shown in FIG. 4. Alternatively, the biosensor was dipped into the incubated solution for electrochemical measurement. The electrochemical measurement was carried out at the +0.25V vs. the Ag/AgCl reference electrode for 120 seconds. The current measured for each sample is shown in FIG. 5. Data in FIGS. 5 and 6 demonstrate that the current measured from the biosensor fits into a linear model with the HbA1c percentage in the blood sample, and the biosensor and the methods can be used for determination of the percentage of glycated hemoglobin without a separate measurement of total hemoglobin.

Example 2

Electrochemical Sensing of HbA1c Using a Biosensor with a Capillary Fill Device

The biosensor described in Example 1 was laminated manually to form a capillary-fill device. See FIG. 4.

Figure 7:
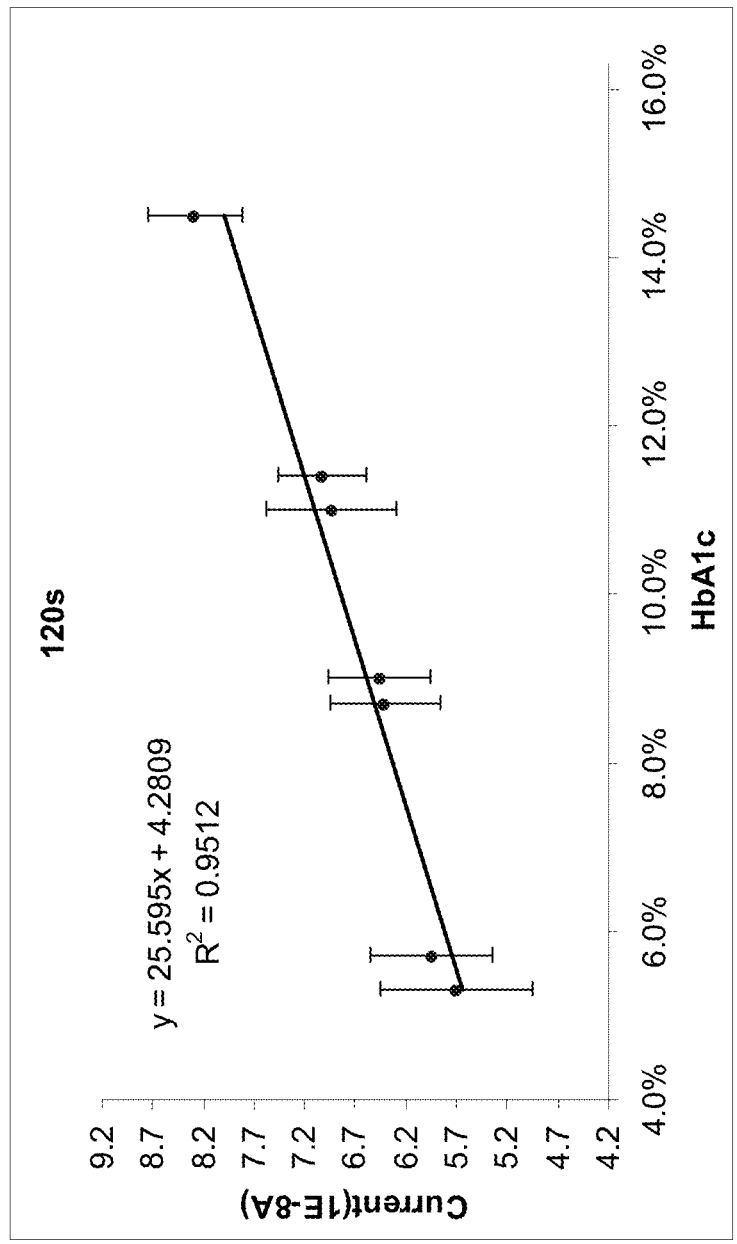
FIG. 7 shows amperometry of blood samples with known HbA1c percentages. The biosensor has a capillary-fill microchannel created by lamination, and was dipped into the lysed blood samples for a few seconds and then used for electrochemical measurement.

The biosensor was dipped into the incubated solution described in Example 1 for a few seconds to fill the micro-channel with the blood lysate through capillary action. The biosensor is then used for electrochemical measurement. The electrochemical measurement was carried out at +0.25V vs. the Ag/AgCl reference for 120 seconds. The current measured for each sample is shown in FIG. 7. Data in FIG. 7 demonstrate that the current measured from the biosensor fits into a linear model with the HbA1c percentage in the blood sample, and the biosensor and the methods can be used for determination of percentage of glycated hemoglobin without a separate measurement of total hemoglobin.

Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention, which is delineated by the appended claims.

The claimed invention is:

1. A method of measuring percentage of glycated hemoglobin (HbA1c) in a sample, comprising:
   a) applying a blood sample to a sample receiving well of an electrode device, wherein the blood sample has been treated with 1) a lysing buffer which releases hemoglobin from red blood cells in the blood sample; 2) a first oxidizing agent which selectively oxidizes a low molecular weight reducing substance 3) a second oxidizing agent which selectively oxidizes a high molecular weight reducing substance, and 4) a protease which digests glycated hemoglobin into glycated peptides or glycated amino acids;
   wherein the electrode device comprises:
   i) an electrode support;
   ii) a working electrode placed on the electrode support, wherein a fructosyl amino acid oxidase is placed on or near the working electrode;
   iii) a counter electrode placed on the electrode support;
   iv) a reference electrode placed on the electrode support, wherein the working, counter and reference electrodes are spaced from each other;
   wherein the working electrode and/or the counter electrode further comprise a catalyst which catalyzes the redox reaction of hydrogen peroxide; and
   v) an insulation/covering layer defining an enclosed space over the working electrode, the counter electrode, and the reference electrode, wherein said insulation/covering layer forms a well for receiving a sample, wherein the sample well is located on the electrodes or near the electrodes;
   wherein (i) the second oxidizing agent is a tetrazolium salt which is 2-(4-iodophenyl)-3-(2,4-dinitrophenyl)-5-(2,4-disulfophenyl)-2H-tetrazolium monosodium salt or 2-(4-iodophenyl)-3-(4-nitrophenyl)-5-(2,4-disulfophenyl)-2H-tetrazolium monosodium salt; (ii) the fructosyl amino acid oxidase comprises the amino acid sequence of SEQ ID NO:1; or (iii) the protease generates a glycated peptide from about 2 to about 30 amino acid residues;
   b) applying an electrical potential between the working electrode and the reference electrode suitable for monitoring the hydrogen peroxide generated from the fructosyl amino acid oxidase-catalyzed reaction; and
   c) measuring an electrical current between the working electrode and the counter electrode or a charge passed at the working electrode;
   whereby the percentage of glycated hemoglobin in the sample is determined based on the measured current or charge as compared to a reference without measuring the total hemoglobin in the blood sample separately.

2. The method of claim 1, wherein the hydrogen peroxide generated by the fructosyl amino acid oxidase-catalyzed reaction is electrochemically detected directly or indirectly via a mediator or a catalyst.

3. The method of claim 1, wherein the electrical potential is applied between the working electrode and the reference electrode in a time delayed manner.

4. The method of claim 1, wherein the reference is a calibration curve.

5. The method of claim 1, wherein the electrode device further comprises a capillary-fill channel for receiving a sample through capillary action, wherein one end of the channel is in contact with the working electrode.

6. The method of claim 1, wherein the working electrode and the counter electrode further comprise a mediator which shuttles electrons between the hydrogen peroxide generated from said fructosyl amino acid oxidase-catalyzed reaction and the working electrode to create a current representative of the amount of the glycated hemoglobin in the sample.

7. The method of claim 6, wherein the mediator comprises one or more agents selected from the group consisting of ferrocene, Prussian Blue, metal phthalocyonine, and tetrathiafulvalene (TTF).

8. The method of claim 1, wherein the catalyst comprises one or more agents selected from the group consisting of Ir-carbon, Rh-carbon, and Ru-carbon.

9. The method of claim 8, wherein said Ir-carbon, Rh-carbon, and Ru-carbon are nanoparticles.

10. The method of claim 1, wherein the fructosyl amino acid oxidase is formulated in a matrix and is placed on or near the working electrode.

11. The method of claim 10, wherein the matrix comprises an enzyme immobilizing agent and a thickening polymer.

12. The method of claim 1, wherein the electrode device further comprises a sample transfer path between said sample well and said working electrode.

13. The method of claim 1, wherein the working electrode and/or the counter electrode comprise a metallized carbon selected from the group consisting of Ir-carbon, Rh-carbon, and Ru-carbon.

14. The method of claim 13, wherein Ir-carbon, Rh-carbon, and Ru-carbon are nanoparticles.

15. The method of claim 1, wherein the reference electrode is Ag/AgCl.

16. The method of claim 1, wherein the electrodes are screen-printed using thick film technology or using thin film lithography.

17. The method of claim 1, wherein the first oxidizing agent is selected from the group consisting of Dess-Martin periodinane, N-ethyl maleimide, sodium iodoacetate, sodium periodate, and Chloramine-T.

18. The method of claim 1, wherein the tetrazolium salt is 2-(4-iodophenyl)-3-(2,4-dinitrophenyl)-5-(2,4-disulfophenyl)-2H-tetrazolium monosodium salt or 2-(4-iodophenyl)-3-(4-nitrophenyl)-5-(2,4-disulfophenyl)-2H-tetrazolium monosodium salt.

19. The method of claim 1, wherein the fructosyl amino acid oxidase comprises the amino acid sequence of SEQ ID NO:1.

20. The method of claim 1, wherein the protease generates a glycated peptide from about 2 to about 30 amino acid residues.

21. A method of measuring percentage of glycated hemoglobin (HbA1c) in a sample, comprising:
   a) applying a blood sample to a sample receiving well of an electrode device; wherein the electrode device comprises:
   i) an electrode support;
   ii) a working electrode placed on the electrode support, wherein a fructosyl amino acid oxidase is placed on or near the working electrode;
   iii) a counter electrode placed on the electrode support;
   iv) a reference electrode placed on the electrode support, wherein the working, counter and reference electrodes are spaced from each other;
   wherein the working electrode and/or the counter electrode further comprise a catalyst which catalyzes the redox reaction of hydrogen peroxide; and
   v) an insulation/covering layer defining an enclosed space over the working electrode, the counter electrode, and the reference electrode, wherein said insulation/covering layer forms a well for receiving a sample, wherein the sample well is located on the electrodes or near the electrodes, and contains a first oxidizing agent which selectively oxidizes a low molecular weight reducing substance, a second oxidizing agent which selectively oxidizes a high molecular weight reducing substance, one or more proteases which digest glycated hemoglobin into glycated peptides or glycated amino acids, and a detergent that lyses red blood cells in a blood sample and releases hemoglobin; and
   vi) a sample transfer path between said sample well and said working electrode;
   wherein (i) the second oxidizing agent is a tetrazolium salt which is 2-(4-iodophenyl)-3-(2,4-dinitrophenyl)-5-(2,4-disulfophenyl)-2H-tetrazolium monosodium salt or 2-(4-iodophenyl)-3-(4-nitrophenyl)-5-(2,4-disulfophenyl)-2H-tetrazolium monosodium salt; (ii) the fructosyl amino acid oxidase comprises the amino acid sequence of SEQ ID NO:1; or (iii) the protease generates a glycated peptide from about 2 to about 30 amino acid residues;
   b) applying an electrical potential between said working electrode and said reference electrode suitable for monitoring the hydrogen peroxide generated from the fructosyl amino acid oxidase-catalyzed reaction; and
   c) measuring an electrical current between the working electrode and the counter electrode or a charge passed at the working electrode;
   whereby the percentage of glycated hemoglobin in the sample is determined based on the measured current or charge as compared to a reference without measuring the total hemoglobin in the blood sample separately.

22. The method of claim 21, wherein the hydrogen peroxide generated by the fructosyl amino acid oxidase-catalyzed reaction is electrochemically detected directly or indirectly via a mediator or a catalyst.

23. The method of claim 21, wherein the electrical potential is applied between the working electrode and the reference electrode in a time delayed manner.

24. The method of claim 21, wherein the reference is a calibration curve.

25. The method of claim 21, wherein the working electrode and the counter electrode further comprise a mediator which shuttles electrons between the hydrogen peroxide generated from said fructosyl amino acid oxidase-catalyzed reaction and the working electrode to create a current representative of the amount of the glycated hemoglobin in the sample.

26. The method of claim 25, wherein the mediator comprises one or more agents selected from the group consisting of ferrocene, Prussian Blue, metal phthalocyonine, and tetrathiafulvalene (TTF).

27. The method of claim 21, wherein the catalyst comprises one or more agents selected from the group consisting of Ir-carbon, Rh-carbon, and Ru-carbon.

28. The method of claim 27, wherein said Ir-carbon, Rh-carbon, and Ru-carbon are nanoparticles.

29. The method of claim 21, wherein the fructosyl amino acid oxidase is formulated in a matrix and is placed on or near the working electrode.

30. The method of claim 29, wherein the matrix comprises an enzyme immobilizing agent and a thickening polymer.

31. The method of claim 21, wherein the working electrode and/or the counter electrode comprise a metallized carbon selected from the group consisting of Ir-carbon, Rh-carbon, and Ru-carbon.

32. The method of claim 31, wherein Ir-carbon, Rh-carbon, and Ru-carbon are nanoparticles.

33. The method of claim 21, wherein the reference electrode is Ag/AgCl.

34. The method of claim 21, wherein the electrodes are screen-printed using thick film technology or using thin film lithography.

35. The method of claim 21, wherein the first oxidizing agent is selected from the group consisting of Dess-Martin periodinane, N-ethyl maleimide, sodium iodoacetate, sodium periodate, and Chloramine-T.

36. The method of claim 21, wherein the tetrazolium salt is 2-(4-iodophenyl)-3-(2,4-dinitrophenyl)-5-(2,4-disulfophenyl)-2H-tetrazolium monosodium salt or 2-(4-iodophenyl)-3-(4-nitrophenyl)-5-(2,4-disulfophenyl)-2H-tetrazolium monosodium salt.

37. The method of claim 21, wherein the fructosyl amino acid oxidase comprises the amino acid sequence of SEQ ID NO:1.

38. The method of claim 21, wherein the protease generates a glycated peptide from about 2 to about 30 amino acid residues.

39. A method of measuring percentage of glycated hemoglobin (HbA1c) in a sample, comprising:
   a) applying a blood sample to a working electrode of an electrode device, wherein the blood sample has been treated with 1) a lysing buffer which releases hemoglobin from red blood cells in the blood sample; 2) a first oxidizing agent which selectively oxidizes a low molecular weight reducing substance if the first oxidizing agent is not placed on or near the working electrode, or a second oxidizing agent which selectively oxidizes a high molecular weight reducing substance if the second oxidizing agent is not placed on or near the working electrode, and 3) a protease which digests glycated hemoglobin into glycated peptides or glycated amino acids;
   wherein the electrode device comprises:
   i) an electrode support;
   ii) a working electrode placed on the electrode support, wherein a fructosyl amino acid oxidase is placed on or near the working electrode, and wherein a first oxidizing agent which selectively oxidizes a low molecular weight reducing substance or a second oxidizing agent which selectively oxidizes a high molecular weight reducing substance is placed on or near the working electrode;
   iii) a counter electrode placed on the electrode support; and iv) a reference electrode placed on the electrode support, wherein the working, counter and reference electrodes are spaced from each other;

wherein (i) the second oxidizing agent is a tetrazolium salt which is 2-(4-iodophenyl)-3-(2,4-dinitrophenyl)-5-(2,4-disulfophenyl)-2H-tetrazolium monosodium salt or 2-(4-iodophenyl)-3-(4-nitrophenyl)-5-(2,4-disulfophenyl)-2H-tetrazolium monosodium salt; (ii) the fructosyl amino acid oxidase comprises the amino acid sequence of SEQ ID NO:1; or (iii) the protease generates a glycated peptide from about 2 to about 30 amino acid residues;

b) applying an electrical potential between said working electrode and said reference electrode suitable for monitoring the hydrogen peroxide generated from the fructosyl amino acid oxidase-catalyzed reaction; and c) measuring an electrical current between the working electrode and the counter electrode or a charge passed at the working electrode;

whereby the percentage of glycated hemoglobin in the sample is determined based on the measured current or charge as compared to a reference without measuring the total hemoglobin in the blood sample separately.

40. The method of claim 39, wherein the treated blood sample is pipetted onto the working electrode.

41. The method of claim 39, wherein the electrode device comprises the capillary-fill channel for receiving a sample through capillary action and one end of the channel is in contact with the working electrode, and wherein the treated blood sample is applied to the working electrode through a capillary-fill channel.

42. The method of claim 39, wherein the working electrode and the counter electrode further comprise a mediator which shuttles electrons between the hydrogen peroxide generated from said fructosyl amino acid oxidase-catalyzed reaction and the working electrode to create a current representative of the amount of the glycated hemoglobin in the sample.

43. The method of claim 42, wherein the mediator comprises one or more agents selected from the group consisting of ferrocene, Prussian Blue, metal phthalocyonine, and tetrathiafulvalene (TTF).

44. The method of claim 39, wherein the working electrode and/or the counter electrode further comprise a catalyst which catalyzes the redox reaction of hydrogen peroxide.

45. The method of claim 44, wherein the catalyst comprises one or more agents selected from the group consisting of Ir-carbon, Rh-carbon, and Ru-carbon.

46. The method of claim 45, wherein said Ir-carbon, Rh-carbon, and Ru-carbon are nanoparticles.

47. The method of claim 39, wherein the fructosyl amino acid oxidase is formulated in a matrix and is placed on or near the working electrode.

48. The method of claim 47, wherein the matrix comprises an enzyme immobilizing agent and a thickening polymer.

49. The method of claim 39, wherein the working electrode and/or the counter electrode comprise a metallized carbon selected from the group consisting of Ir-carbon, Rh-carbon, and Ru-carbon.

50. The method of claim 49, wherein Ir-carbon, Rh-carbon, and Ru-carbon are nanoparticles.

51. The method of claim 39, wherein the reference electrode is Ag/AgCl.

52. The method of claim 39, wherein the electrodes are screen-printed using thick film technology or using thin film lithography.

53. The method of claim 39, wherein the first oxidizing agent is selected from the group consisting of Dess-Martin periodinane, N-ethyl maleimide, sodium iodoacetate, sodium periodate, and Chloramine-T.

54. The method of claim 39, wherein the tetrazolium salt is 2-(4-iodophenyl)-3-(2,4-dinitrophenyl)-5-(2,4-disulfophenyl)-2H-tetrazolium monosodium salt or 2-(4-iodophenyl)-3-(4-nitrophenyl)-5-(2,4-disulfophenyl)-2H-tetrazolium monosodium salt.

55. The method of claim 39, wherein the fructosyl amino acid oxidase comprises the amino acid sequence of SEQ ID NO:1.

56. The method of claim 39, wherein the protease generates a glycated peptide from about 2 to about 30 amino acid residues.

* * * * *

SEQUENCE LISTING

```
<160> NUMBER OF SEQ ID NOS: 1

<210> SEQ ID NO 1
<211> LENGTH: 472
<212> TYPE: PRT
<213> ORGANISM: Artificial Sequence
<220> FEATURE:
<223> OTHER INFORMATION: Synthetic Construct

<400> SEQUENCE: 1

Met Gly Gly Ser Gly Asp Asp Asp Asp Leu Ala Leu Ala Val Thr Lys
```

-continued

```
            1               5                  10                 15
          Ser Ser Ser Leu Leu Ile Val Gly Ala Gly Thr Trp Gly Thr Ser Thr
                      20                  25                  30

Ala Leu His Leu Ala Arg Arg Gly Tyr Thr Asn Val Thr Val Leu Asp
                      35                  40                  45

Pro Tyr Pro Val Pro Ser Ala Ile Ser Ala Gly Asn Asp Val Asn Lys
                      50                  55                  60

Val Ile Ser Ser Gly Gln Tyr Ser Asn Asn Lys Asp Glu Ile Glu Val
          65                  70                  75                  80

Asn Glu Ile Leu Ala Glu Glu Ala Phe Asn Gly Trp Lys Asn Asp Pro
                      85                  90                  95

Leu Phe Lys Pro Tyr Tyr His Asp Thr Gly Leu Leu Met Ser Ala Cys
                      100                 105                 110

Ser Gln Glu Gly Leu Asp Arg Leu Gly Val Arg Val Arg Pro Gly Glu
                      115                 120                 125

Asp Pro Asn Leu Val Glu Leu Thr Arg Pro Glu Gln Phe Arg Lys Leu
                      130                 135                 140

Ala Pro Glu Gly Val Leu Gln Gly Asp Phe Pro Gly Trp Lys Gly Tyr
          145                 150                 155                 160

Phe Ala Arg Ser Gly Ala Gly Trp Ala His Ala Arg Asn Ala Leu Val
                      165                 170                 175

Ala Ala Ala Arg Glu Ala Gln Arg Met Gly Val Lys Phe Val Thr Gly
                      180                 185                 190

Thr Pro Gln Gly Arg Val Val Thr Leu Ile Phe Glu Asn Asn Asp Val
                      195                 200                 205

Lys Gly Ala Val Thr Gly Asp Gly Lys Ile Trp Arg Ala Glu Arg Thr
          210                 215                 220

Phe Leu Cys Ala Gly Ala Ser Ala Gly Gln Phe Leu Asp Phe Lys Asn
          225                 230                 235                 240

Gln Leu Arg Pro Thr Ala Trp Thr Leu Val His Ile Ala Leu Lys Pro
                      245                 250                 255

Glu Glu Arg Ala Leu Tyr Lys Asn Ile Pro Val Ile Phe Asn Ile Glu
                      260                 265                 270

Arg Gly Phe Phe Phe Glu Pro Asp Glu Glu Arg Gly Glu Ile Lys Ile
                      275                 280                 285

Cys Asp Glu His Pro Gly Tyr Thr Asn Met Val Gln Ser Ala Asp Gly
                      290                 295                 300

Thr Met Met Ser Ile Pro Phe Glu Lys Thr Gln Ile Pro Lys Glu Ala
          305                 310                 315                 320

Glu Thr Arg Val Arg Ala Leu Leu Lys Glu Thr Met Pro Gln Leu Ala
                      325                 330                 335

Asp Arg Pro Phe Ser Phe Ala Arg Ile Cys Trp Cys Ala Asp Thr Ala
                      340                 345                 350

Asn Arg Glu Phe Leu Ile Asp Arg His Pro Gln Tyr His Ser Leu Val
                      355                 360                 365

Leu Gly Cys Gly Ala Ser Gly Arg Gly Phe Lys Tyr Leu Pro Ser Ile
                      370                 375                 380

Gly Asn Leu Ile Val Asp Ala Met Glu Gly Lys Val Pro Gln Lys Ile
          385                 390                 395                 400

His Glu Leu Ile Lys Trp Asn Pro Asp Ile Ala Ala Asn Arg Asn Trp
                      405                 410                 415

Arg Asp Thr Leu Gly Arg Phe Gly Gly Pro Asn Arg Val Met Asp Phe
                      420                 425                 430
```

```
His Asp Val Lys Glu Trp Thr Asn Val Gln Tyr Arg Asp Ile Ser Lys
            435                 440                 445

Leu Lys Gly Glu Leu Glu Gly Leu Pro Ile Pro Asn Pro Leu Leu Arg
    450                 455                 460

Thr Gly His His His His His
465                 470
```